US011761952B2

(12) United States Patent
Liu et al.

(10) Patent No.: US 11,761,952 B2
(45) Date of Patent: Sep. 19, 2023

(54) EXOSOME-TOTAL-ISOLATION-CHIP (EXOTIC) DEVICE FOR ISOLATION OF EXOSOME-BASED BIOMARKERS

(71) Applicant: The Board of Trustees of the Leland Stanford Junior University, Stanford, CA (US)

(72) Inventors: Fei Liu, Mountain View, CA (US); Utkan Demirci, Stanford, CA (US); Sanjiv Sam Gambhir, Stanford, CA (US); Viswam S. Nair, Tampa, FL (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 278 days.

(21) Appl. No.: 17/345,968

(22) Filed: Jun. 11, 2021

(65) Prior Publication Data
US 2021/0311025 A1  Oct. 7, 2021

Related U.S. Application Data

(62) Division of application No. 16/073,577, filed as application No. PCT/US2017/016035 on Feb. 1, 2017, now Pat. No. 11,073,511.
(Continued)

(51) Int. Cl.
*G01N 33/50* (2006.01)
*B01L 3/00* (2006.01)
*G01N 33/53* (2006.01)

(52) U.S. Cl.
CPC ...... *G01N 33/5091* (2013.01); *B01L 3/50273* (2013.01); *B01L 3/502715* (2013.01);
(Continued)

(58) Field of Classification Search
CPC .......... G01N 33/5091; G01N 33/5005; G01N 2035/00465; G01N 2035/00475; B01L 3/502761; B01L 3/5027
See application file for complete search history.

(56) References Cited

U.S. PATENT DOCUMENTS 11,073,511 B2 * 7/2021 Liu .................. B01L 3/502715
2009/0258379 A1   10/2009 Klein et al.
(Continued)

FOREIGN PATENT DOCUMENTS

WO   2013158203 A1   10/2013
WO   2015045666 A1    4/2015
(Continued)

OTHER PUBLICATIONS

PCT International Search Report and Written Opinion, PCT/US2017/016035, May 23, 2017, 14 pages.

*Primary Examiner* — Brian J. Sines
(74) *Attorney, Agent, or Firm* — Quarles & Brady LLP

(57) ABSTRACT

A device ("the ExoTIC device") for the isolation of extracellular vesicles from an extracellular vesicle-containing sample in which the sample is flowed through a membrane in a flow chamber to capture and purify the extracellular vesicles on the membrane. The extracellular vesicles may be washed and collected and utilized in any one of a number of ways including, but not limited to, identifying biomarkers of a disease, identifying the presence of a biomarker in a patient to determine whether a patient has a disease, and therapeutically treating existing diseases by re-introducing the extracellular vesicles, potentially modified, back into a body.

11 Claims, 16 Drawing Sheets

Related U.S. Application Data

(60) Provisional application No. 62/289,795, filed on Feb. 1, 2016.

(52) U.S. Cl.
CPC ........ B01L 3/502761 (2013.01); G01N 33/50 (2013.01); G01N 33/5005 (2013.01); G01N 33/5308 (2013.01); *G01N 2800/52* (2013.01); *G01N 2800/56* (2013.01)

(56) References Cited

U.S. PATENT DOCUMENTS

| | | |
|---|---|---|
| 2010/0184046 A1 | 7/2010 | Klass et al. |
| 2012/0070858 A1 | 3/2012 | Contreras et al. |
| 2013/0273544 A1 | 10/2013 | Vlassov et al. |
| 2015/0141634 A1 | 5/2015 | Mitsuhashi |
| 2016/0230235 A1 | 8/2016 | Ichiki et al. |
| 2016/0333338 A1 | 11/2016 | Haj-Ahmad |
| 2016/0354313 A1 | 12/2016 | De Beer |
| 2017/0014450 A1 | 1/2017 | Joyce et al. |
| 2018/0028687 A1 | 2/2018 | Selaru et al. |
| 2018/0327714 A1 | 11/2018 | Stice et al. |
| 2020/0166524 A1 | 5/2020 | De Kleijn et al. |

FOREIGN PATENT DOCUMENTS

| | | |
|---|---|---|
| WO | 2015120150 A1 | 8/2015 |
| WO | 2015131153 A1 | 9/2015 |

\* cited by examiner

EXOSOME-TOTAL-ISOLATION-CHIP (EXOTIC) DEVICE FOR ISOLATION OF EXOSOME-BASED BIOMARKERS

CROSS-REFERENCE TO RELATED APPLICATIONS

This application is a divisional of U.S. patent application Ser. No. 16/073,577 filed Jul. 27, 2018, which represented the U.S. national stage entry of International Application No. PCT/US2017/016035 filed Feb. 1, 2017, which claims the benefit of U.S. Provisional Patent Application No. 62/289,795 entitled "Exosome-Total-Isolation-Chip (ExoTIC) Device for Identification of Exosome-Based Biomarkers" filed Feb. 1, 2016, the contents of which are incorporated by reference herein in its entirety for all purposes.

STATEMENT OF FEDERALLY SPONSORED RESEARCH OR DEVELOPMENT

This invention was made with Government support under contract W81XWH-16-1-0200 awarded by the U.S. Army Medical Research Materiel Command and under contracts CA199075 and DE024971 awarded by the National Institutes of Health. The Government has certain rights in the invention.

BACKGROUND

This disclosure relates to the identification of extracellular vesicle or exosome-based biomarkers and, in particular, to devices and methods of using these devices for isolation of extracellular vesicle or exosome-based biomarkers.

Exosomes, which are small (generally, 30-180 nm) cell-derived vesicles, are abundantly secreted by different types of cells into the extracellular fluids such as blood, urine and saliva, and circulation. As used herein throughout this disclosure, the term "extracellular vesicle" includes the term "exosome" and all other types of extracellular vesicles. Various tumor types release exosomes into the blood that are enriched with DNA, reflecting the mutational status of the originating cancer cell, mRNA, miRNA and proteins, with important roles in disease onset, progression and metastasis. Therefore, circulating tumor-derived exosomes hold great potential as novel biomarkers for noninvasive cancer detection.

As one example, lung cancer is the predominant form of cancer in the United States because it often escapes diagnoses at an early stage. Blood biomarkers for lung cancer have raised great expectations in their clinical applications for early diagnosis, prognosis, and therapeutic responses. However, low abundance and poor specificity of these conventional serum markers, such as carcinoembryonic antigen (CEA) and squamous cell carcinoma antigen (SCC), have hampered their implementation. Identifying reliable biomarkers for the early detection of lung cancer will thus significantly improve the survival rate of patients. Thus, exosome-derived biomarkers provide a promising avenue for early lung cancer diagnoses and improved prognosis.

SUMMARY OF THE INVENTION

To date, translating exosomes as cancer biomarkers into clinical practice has proven challenging as a reliable source for diagnosis. Existing exosome purification technologies (ultracentrifugation, multi-step filtration, antibody conjugated magnetic beads or polyethylene glycol based precipitation, see the left three panels on the bottom of FIG. 1) are often expensive, time-consuming, require large sample volumes and frequent manual handling, and/or result in poor yields and unpredictable purity of exosome preparations, especially when derived from clinical plasma samples. This inability to efficiently purify and isolate exosomes has proven to be a major impediment to the application of exosomes for drug delivery and diagnostics.

Here, an innovative exosome total isolation chip (herein referred to as "ExoTIC") is disclosed that can isolate large amounts of pure exosomal preparations from a wide range of clinical bio-fluids, which can be easily implemented in the clinic, and that can facilitate the identification of biomarkers (in combination with genomic analysis) of disease onset and progression. Uniquely, this cost-effective, single step, size based filtration device allows rapid, high yield and high purity isolation of exosomes. It can be applied universally to study a wide range of body fluids, including blood and cancer types. The implementation of the ExoTIC device has the potential to transform the field of clinical biomarker discovery and the diagnosis, prognosis and therapeutic strategies, such as, for example, lung cancer in which the ability to provide early diagnosis and monitor disease progression would improve patient outcomes.

According to one aspect, a method of processing an extracellular vesicle-containing sample using a device for extracellular vesicle isolation is disclosed. The extracellular vesicle-containing sample is flowed through a flow chamber of the device for extracellular vesicle isolation under an applied fluid pressure. The device has an inlet and an outlet which are placed in fluid communication with one another via the flow chamber. The device further has a membrane through which the extracellular vesicle-containing sample must flow as the extracellular vesicle-containing sample flows from the inlet to the outlet. Extracellular vesicles are isolated from the extracellular vesicle-containing sample on the membrane with the membrane collecting at least some of the extracellular vesicles on it while permitting a remainder of the extracellular vesicle-containing sample to flow through the membrane towards the outlet.

It is contemplated that extracellular vesicles may be exosomes, specifically, and that the exosomes are isolated while all, some, or none of the other extracellular vesicles are isolated.

In some forms, the extracellular vesicle-containing sample may be culture media, blood, plasma, urine, saliva, lavage, or serum. However, it is contemplated that an extracellular vesicle-containing biofluid may be used under suitable processing conditions (flow rate, pore diameter of the membrane and any supporting backing layers, and so forth).

In some forms, the step of flowing may involve injecting the extracellular vesicle-containing sample into the inlet using a syringe. In some cases, the syringe may be controllably operated using a syringe pump.

In different forms, the membrane may have differently selected pore diameters (which may be selected in part to capture the extracellular vesicles of most interest to a particular assay). In some forms, the membrane may have an average pore diameter below 200 nm and in some instances the average pore diameter may be as small as 30 nm or 50 nm.

In some forms, the device may further include a supportive backing layer or layers between the membrane and the outlet to assist the membrane in retaining its form under the applied fluid pressure. The supportive backing layers may include a paper pad and/or an additional filter such as a PES filter.

In some forms, the step of flowing the extracellular vesicle-containing sample through a flow chamber of the device for extracellular vesicle isolation under an applied fluid pressure may involve rotating the device to alter an orientation of the inlet relative to the outlet to facilitate collection of the extracellular vesicles isolated on the membrane.

In some forms, the method may further include the step of washing the extracellular vesicles collected on the membrane by flowing a washing fluid over the extracellular vesicles collected on the membrane. This may help to remove, for example, free proteins, nucleic acids, and cell debris.

Still yet, in some forms, the method may further comprise the step of collecting the extracellular vesicles from the membrane. This may be done, for example, using a pipette. The collected extracellular vesicles may be evaluated for various purposes. In some instances, the collected extracellular vesicles may be aggregated across a plurality of samples of different patients to identify shared biomarkers across the plurality of collected extracellular vesicles in which the shared biomarkers are indicative of a shared disease of the patients. Still yet, a profile (e.g., one or more of a quantity, a size, a morphology or so forth) of the extracellular vesicles collected from the membrane may be compared to a known profile associated with a disease of a patient in order to diagnose a patient associated with the sample with a disease. In some instances, this may involve not just identifying the presences of a disease (or lack thereof), but may involve identifying a stage or severity of the disease. As another example of a type of evaluation to be performed, a drug may be administered to the collected extracellular vesicles from the membrane and a drug response to the drug may be determined and resistance to the extracellular vesicles may be monitored over time.

In some forms, the method may involve placing several devices for extracellular vesicle isolation in series with one another, connecting the outlet of one of the devices to the inlet of another one of the devices to form a modular device, in which each of the several devices for extracellular vesicle isolation has a membrane with a different porosity, and then flowing the extracellular vesicle-containing sample through the modular device thereby resulting in size-based separation of the extracellular vesicles.

Still yet, in some forms, the extracellular vesicles collected on the membrane may be subsequently utilized in a therapeutic treatment.

According to another aspect, a device for isolation of extracellular vesicles from an extracellular vesicle-containing sample is disclosed. The device includes a flow chamber having an inlet and an outlet which are placed in fluid communication with one another by the flow chamber. The device further includes a membrane disposed in the flow chamber such that a fluid flowing from the inlet to the outlet through the flow chamber must pass through the membrane. The membrane is adapted to collect extracellular vesicles from the extracellular vesicle-containing sample thereon while permitting a remainder of the extracellular vesicle-containing sample to flow through the flow chamber to the outlet.

It is contemplated that extracellular vesicles may be exosomes, specifically, and that the exosomes are isolated while all, some, or none of the other extracellular vesicles are isolated.

In some forms, the device may further include a supportive backing layer or layers between the membrane and the outlet. The supportive backing layer(s) may include a paper pad and/or a filter such as a PES filter which are disposed between the membrane and the outlet. In one instance, the PES filter may be positioned between the membrane and the paper pad.

It is contemplated that, in some forms, the device may have a membrane selected to capture particular exosome or types of extracellular vesicles. In some forms, this may involve using a membrane with a particular porosity or pore size. It is contemplated that the membrane may have a porosity with an average pore diameter of 30 nm, 50 nm, 80 nm, 100 nm, 200 nm, 1000 nm or 5000 nm, for example. In some instances, where there is a filter past the membrane with supporting function, the average pore diameter of the filter may be larger than the membrane (e.g., the filter may gave an average pore diameter of 200 nm) so as not to further capture smaller particles beyond the membrane.

In some forms, the flow chamber may be defined by a pair of opposing plates fastened together to secure the membrane in place therebetween in which one of the pair of opposing plates provides the inlet and the other of pair of opposing plates provides the outlet. A pair of gaskets may be positioned between the plates in which the membrane is secured between the pair of gaskets.

According to still another aspect, a modular device for isolation of extracellular vesicles from an extracellular vesicle-containing sample is disclosed. The modular device includes several devices for extracellular vesicle isolation as described above and herein in series with one another, connecting the outlet of one of the devices to the inlet of another one of the devices. Each of the several devices for extracellular vesicle isolation has a membrane with a different porosity or pore diameter than at least some of the others.

In some forms, it is contemplated that the membranes of each of the several devices may have decreasing average pore diameters from the inlet of a first device to the outlet of the last device.

One having ordinary skill in the art that the various features and steps claimed herein and/or described herein may be employed in combination with one other, where workable, and in various permutations with one another.

It is contemplated that there are many potential advantages of the ExoTIC device over existing methods, devices, and/or materials. In comparison to traditional means, the ExoTIC device is both time and labor saving and very cost effective. Still yet, as will be discussed below, it yields greater amount of exosomes from a sample that other methods. It is usable with a wide range of sample volumes, including from 10 μL to 50 mL and is suitable for use on all types of biological samples (including, but not limited to, plasma, serum, urine, saliva, culture media, and ascitic fluid). The device can process in series and parallel configurations larger volumes than 50 mL. Still further, it is contemplated that it may be integrated with microfluidic chip devices. Moreover, because of the manner in which it operates the ExoTIC can provide size-specific exosome isolation.

These and still other advantages of the invention will be apparent from the detailed description and drawings. What follows is merely a description of a preferred embodiment of the present invention. To assess the full scope of the invention, the claims should be looked to as the preferred embodiment is not intended to be the only embodiment within the scope of the claims.

BRIEF DESCRIPTION OF THE DRAWINGS

FIG. 4a is an exploded view of the design of ExoTIC device. FIG. 4b is an illustration of ExoTIC device in assembled from the components illustrated in FIG. 4a in which the assembled ExoTIC device is in partial section and a detailed image shows the internal structure of a portion of the assembled ExoTIC device. FIG. 4c illustrates the various materials prepared for fabrication of one ExoTIC device in a non-assembled state, providing detailed dimensions such as thickness, diameter, and pore size. FIG. 4d illustrates stepwise, the fabrication procedure of an ExoTIC device. FIG. 4e is a photograph of the assembled ExoTIC device in using with a 10 mL BD syringe.

FIGS. 7a-7c provide NanoSight and SEM analysis of exosomes isolated using ultracentrifugation method (UC) [FIG. 7a], ExoQuick-TC [FIG. 7b], and an ExoTIC device [FIG. 7c]. FIG. 7d provides a comparison of exosome yield purified from HCC827 lung adenocarcinoma cell culture medium by the ExoTIC device (5 mL), ultracentrifugation (60 mL), and ExoQuick-TC kit (5 mL). FIG. 7e provides a comparison of the mean size of exosomes purified by the three methods as determined by a NanoSight NS300 instrument. FIG. 7f provides a comparison of the total amount of exosomes purified from different volumes of HCC827 cell culture medium using the ExoTIC device. FIG. 7g is a TEM image of exosomes isolated from culture media (HCC827 cell line) using the ExoTIC device.

FIG. 10a shows the design of an ExoTIC device with modular function for isolation of specific size extracellular vesicles. FIG. 10b is a photograph of the ExoTIC modular platform with a number of the devices in series each of the devices having different filter sizes. FIG. 10c illustrates a NanoSight analysis of specific size exosomes from HCC827 culture media. FIGS. 10d and 10e respectively show the amount of different size exosomes isolated from HCC827 culture media and GBM39 culture media.

FIG. 12a shows the yield comparison of exosomes isolated from 500 µL healthy human plasma samples between ultracentrifugation method and an ExoTIC device. FIG. 12b demonstrates the exemplary capability of an ExoTIC device for isolating exosomes from different volume of plasma samples, ranging from 10 to 500 µL. FIGS. 12c and 12d provide yield comparisons of exosome yield isolated from two different 100 µL healthy human plasma samples using the different isolation methodologies. FIGS. 12e and 12f show the comparative mean sizes of human plasma exosomes isolated using the various isolation methods.

FIG. 13a lists the patient information (of patient #19 and patient #25) and sample volume (urine, lavage and plasma) used for exosome isolation. FIG. 13b provides SEM images of exosomes isolated from different samples of patient #19. FIG. 13c provides concentration/size graph of exosomes isolated for various clinical sample types of patient #19 using NanoSight. FIG. 13d provides the amounts of exosomes present in the plasma, urine, and lavage samples of both patient #19 and patient #25. FIG. 13e provides the mean sizes of the exosomes present in the plasma, urine, and lavage samples of both patient #19 and patient #25.

DETAILED DESCRIPTION OF THE INVENTION

Figure 1:
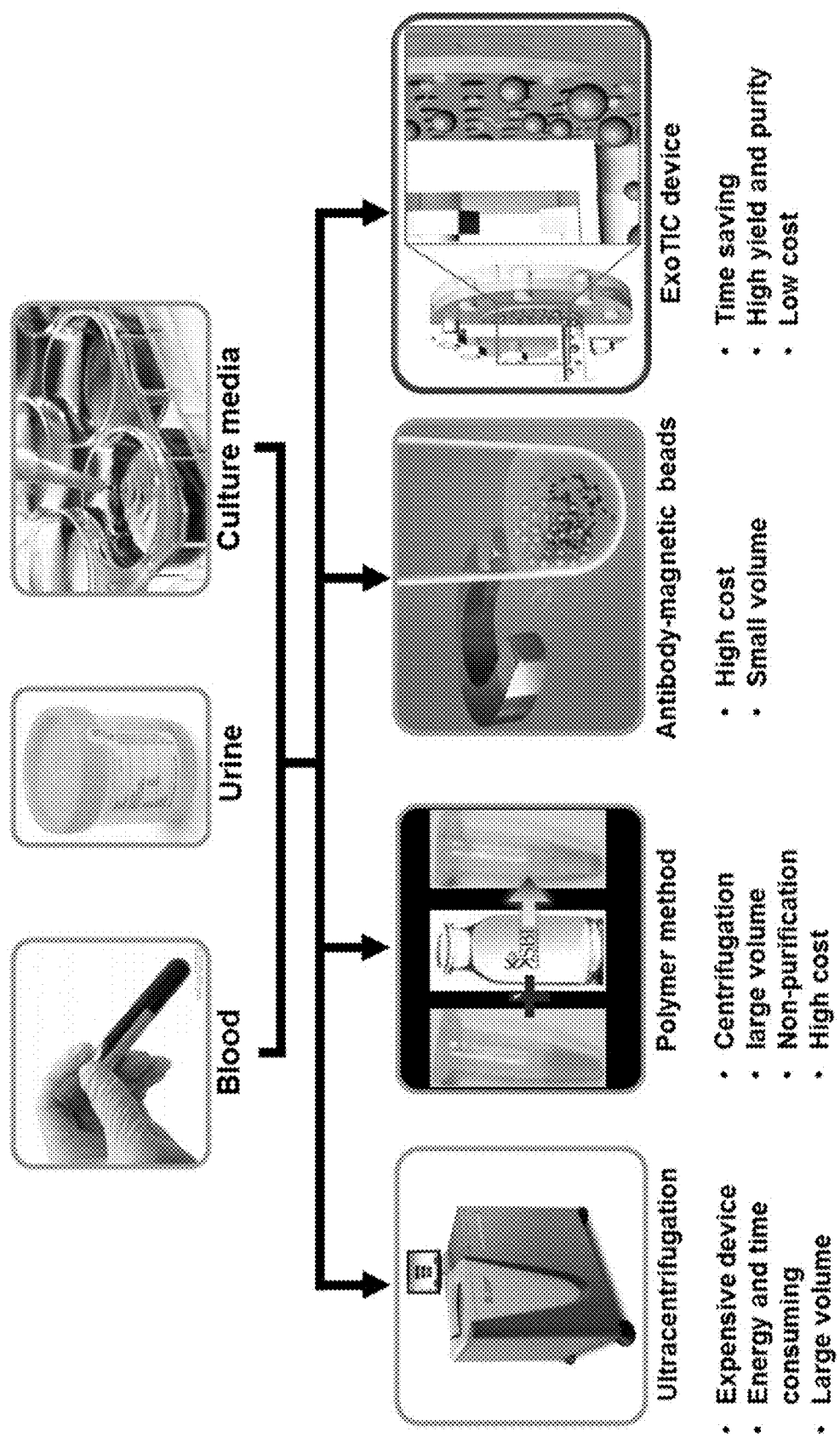
FIG. 1 is an illustration showing exemplary methods of exosome isolation, both old (ultracentrifugation, polymer method, and antibody-magnetic beads) and new (the ExoTIC device) from various exemplary sample inputs (blood, urine, and culture media) and highlighting the various qualities and characteristics of the different isolation methods.

As noted above, exosomes carry biological analytes (for example, proteins, metabolites, and nucleotides) that reflect their cell type of origin. Due to their important role as messengers in cell-cell communication, exosomes are emerging both as candidate biomarkers in liquid biopsies and as targeted drug delivery vehicles for therapeutics. However, a major challenge hindering the routine clinical use of exosomes is the lack of simple and inexpensive, yet robust and reproducible methods for their isolation and enrichment. Table 1 below, provides a brief summary of each of the existing exosome purification technologies and compares them with the ExoTIC device disclosed herein.

TABLE 1

Comparison of different methods for exosome isolation

| Methods | Sample types | Volume | Exo Yield | Exo Purity | Time |
|---|---|---|---|---|---|
| Ultra-centrifugation (UC) | Culture media Ascitic fluid Urine | >30 mL | Low | High | Days |
| Filter method | Culture media | 60 mL | Low | Low | Hours |
| Polyethylene glycol (PEG) | Culture media Plasma/serum Ascitic fluid Urine | 1-5 mL 60-300 µL 1-5 mL 1-5 mL | Low | Low | Hours |
| Antibody-magnetic Beads | Culture media Plasma/serum | 100 µL-1mL | Low | High | Hours |
| ExoTIC device | Culture media | 0.5 mL-50 mL | High | High | Hours |

TABLE 1-continued

Comparison of different methods for exosome isolation

| Methods | Sample types | Volume | Exo Yield | Exo Purity | Time |
|---|---|---|---|---|---|
| | Plasma/serum Lavage/urine/ ascetic fluids | 10 μL-500 μL 1 mL-50 mL | | | |

The innovative and radically different ExoTIC technology has seven non-limiting advantages over the mostly commonly used ultracentrifugation method for exosome purification. The ExoTIC technology is: (1) easy-to-use, (2) rapid, (3) high-throughput, (4) high-yield (more than 90% recovery), (5) highly reproducible, (6) inexpensive (<$10), and (7) able to process clinical samples of both small and large volume with high purity. The ExoTIC technology could potentially become a standard method for exosome purification, allowing comparing data between laboratories. Large amounts of the exosomes purified by the ExoTIC technology may improve our understanding of the roles of exosomes in physiological and pathological conditions such as cancer.

Disclosed herein are exosome total isolation chip ("ExoTIC") devices—an easy-to-use, filter-based separation device that facilitates exosome biomarker analysis through high-yield recovery—and methods relating to the use of this device. In some forms, the ExoTIC device may be designed and fabricated using a poly(methyl methacrylate) and polycarbonate nanoporous membrane for size-based exosome separation, enrichment and purification. The isolation efficiency of the ExoTIC device was validated on cell culture media from different cancer cell lines and human plasma by quantifying exosome yield with NanoSight (a tool available from Malvern Instruments Ltd of Malvern, UK which permits rapid, automated analysis of the size distribution and concentration of nanoparticles from 10 nm to 2000 nm in diameter). Compared to isolation by ultracentrifugation (hereinafter also denoted by "UC" in the text and figures), operation of the ExoTIC devices is not labor intensive, is automatable, and achieves unprecedented high yields from small volumes of clinical samples such as saliva and lavage, where more sample volume is not physically collectible. The exemplary ExoTIC device presented exosome yields four-to-six-fold and more than one thousand-fold higher compared to ultracentrifugation from 1-5 milliliters of culture media and 10-500 microliters of healthy-donor plasma, respectively. For downstream analysis, microRNA profiles of exosomes derived from 10 milliliters of culture media using the ExoTIC device and 60 milliliters of the same culture media using ultracentrifugation were similar in amount and expression levels. The ExoTIC device effectively isolated exosomes from plasma, urine, and bronchoalveolar lavage fluid from patients with non-small cell lung cancer. MicroRNA expression profiling was performed on the exosomes isolated from these clinical samples showing comparable quantification as observed in ultracentrifugation. Overall, the ExoTIC device can simplify exosome recovery and improves yield in a variety of human bio-fluids for exosome-derived biomarker studies with broad applications in multiple cancers and other immunological diseases.

Figure 2:
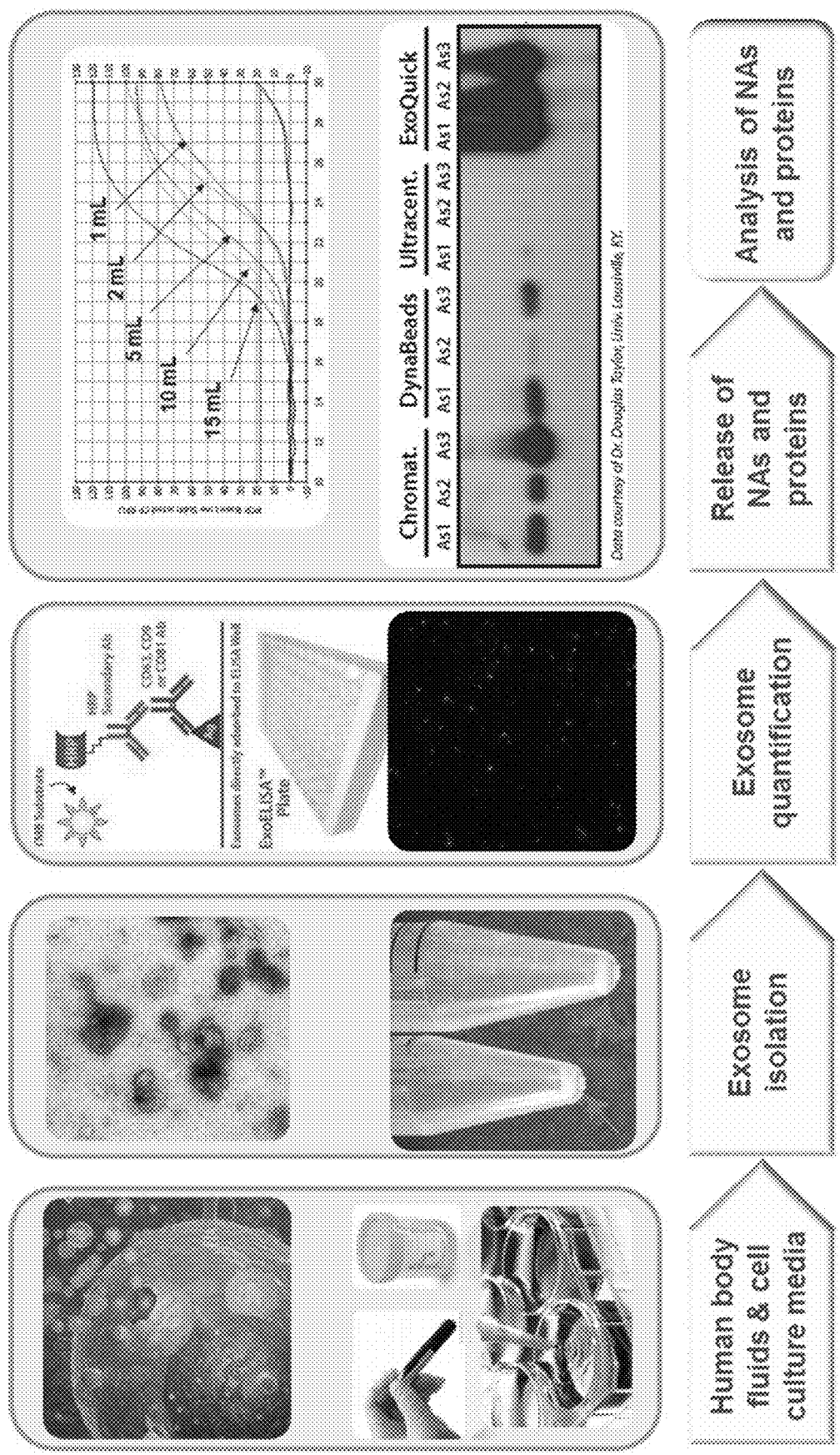
FIG. 2 illustrates a process for exosome isolation, quantification, and analysis.

Looking first at FIG. 2, an overall process for exosome isolation, quantification, and analysis is outlined that is not specific to the ExoTIC device. Generally speaking, exosome-containing samples in the form of human body fluids or cell cultures are obtained and exosomes are isolated from those samples (this may be done using, for example, any of the methodologies—ultracentrifugation, polyethylene glycol based precipitation, antibody conjugated magnetic beads, or use of the ExoTIC device—depicted on the bottom row of panels in of FIG. 1). Then exosomes may then be quantified using conventional process using imaging and enzyme-linked immunosorbent assays (ELISA). The development of nucleic acids and proteins may be utilized to further characterize the isolated exosomes. It should be noted that the method of quantifying and characterizing the isolated exomes is exemplary only and that there may be other ways of quantifying and characterizing the isolated, purified exosomes.

Figure 3:
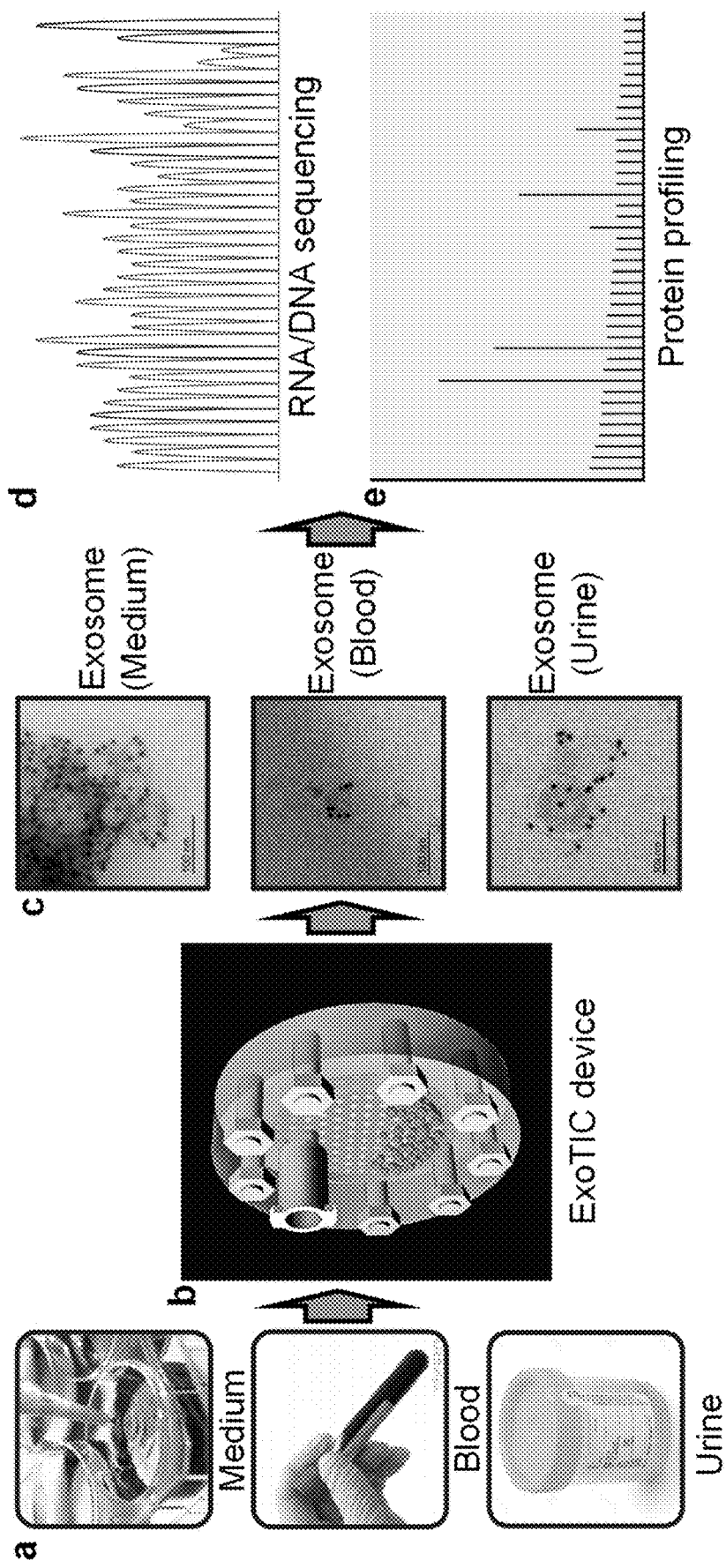
FIG. 3 is a schematic illustration of how the ExoTIC device can be implemented in exosome isolation and biomarker identification from exosome-containing samples.

Turning now to FIG. 3, FIG. 3 is a schematic illustration specifically depicting the integration of the ExoTIC device into the process outlined in FIG. 2 for exosome isolation and biomarker identification. As can be seen, various biofluids (in the exemplary forms of culture media, blood, or urine although other non-illustrated biological fluids, for example, lavage or saliva may also be used) which are exosome-containing samples from FIG. 3a are processed by the ExoTIC device in FIG. 3b, the structure of which will be described in greater detail below, for exosome isolation. FIG. 3c depicts TEM images of exosomes isolated from different types of samples using the ExoTIC device. The isolated exosomes can then be identified or evaluated using next generation sequencing technology (as generally depicted in FIG. 3d) and/or proteomic technology as depicted in FIG. 3e.

The principle of the ExoTIC device for exosome purification is based on size separation. Specifically, the ExoTIC device uses a nanoporous (e.g., pore size of 30 nm), low protein binding filter membrane to selectively retain exosomes (e.g., 30 to 150 nm in diameter) while the contaminating small molecules, such as nucleic acids and proteins originating from the plasma and other body fluids, pass through the membrane and are removed through the outlet. Then, the concentrated exosomes are retrieved from the inlet with high yield (more than 90% recovery). Using this method, exosomes isolated from the body fluids of patients may be obtained and, by observing specific and distinct expression patterns of microRNAs, mRNAs, genomic DNAs, and proteins (using, for example, the processes depicted in FIGS. 3d and 3e or others), unhealthy patients (e.g., those having cancer) may be distinguished from healthy patients by identifying exosomal biomarkers. By identifying the exosomal biomarkers of interest to a particular malady and then looking for those specific biomarkers in patients of unknown health, it is hoped that improved and earlier diagnosis of diseases such as lung cancer may made.

Design and Fabrication of the ExoTIC Device

Figure 4:
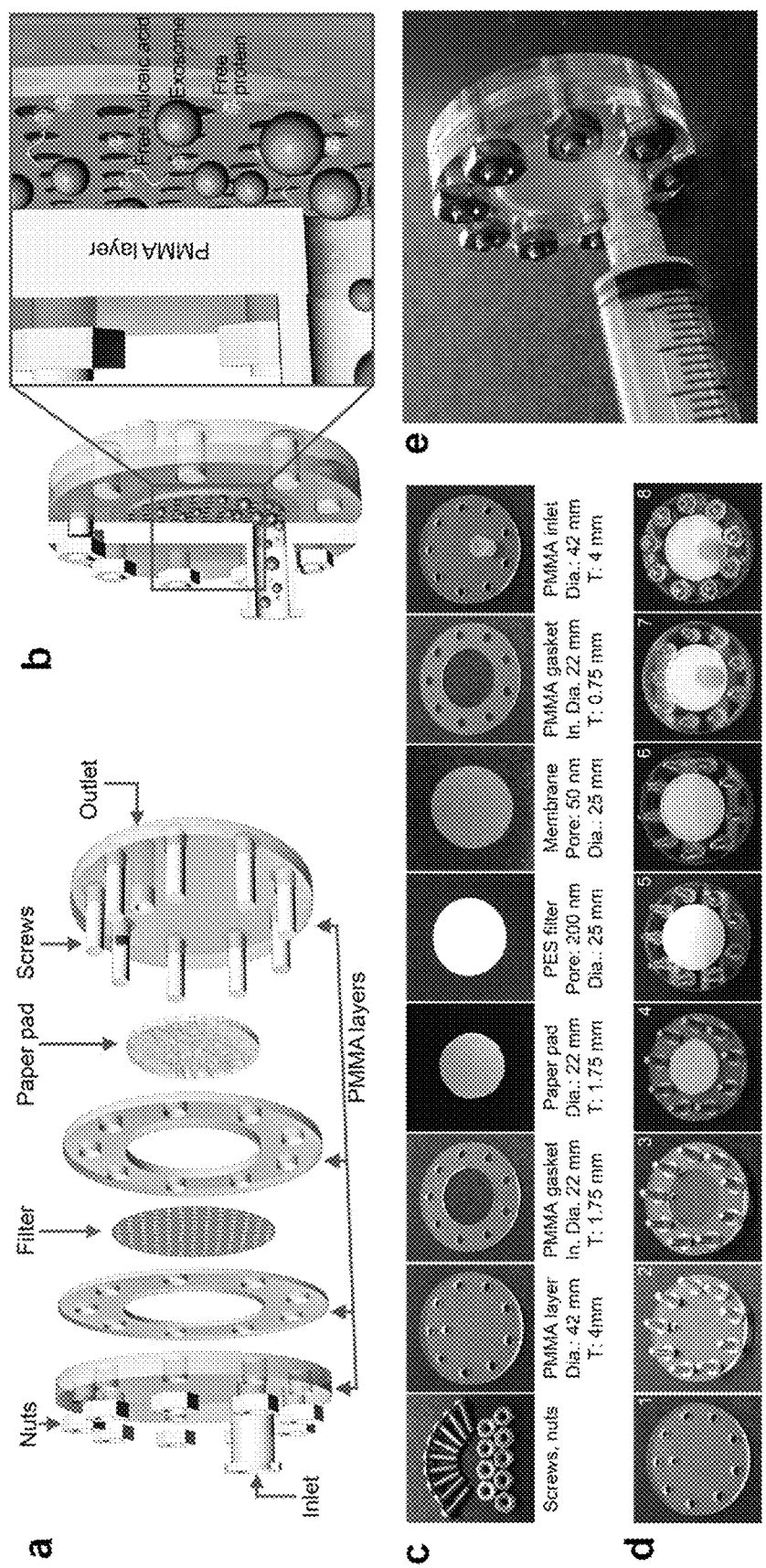
FIG. 4 illustrates the design and fabrication of an exemplary ExoTIC device for exosome isolation.
Figure 5:
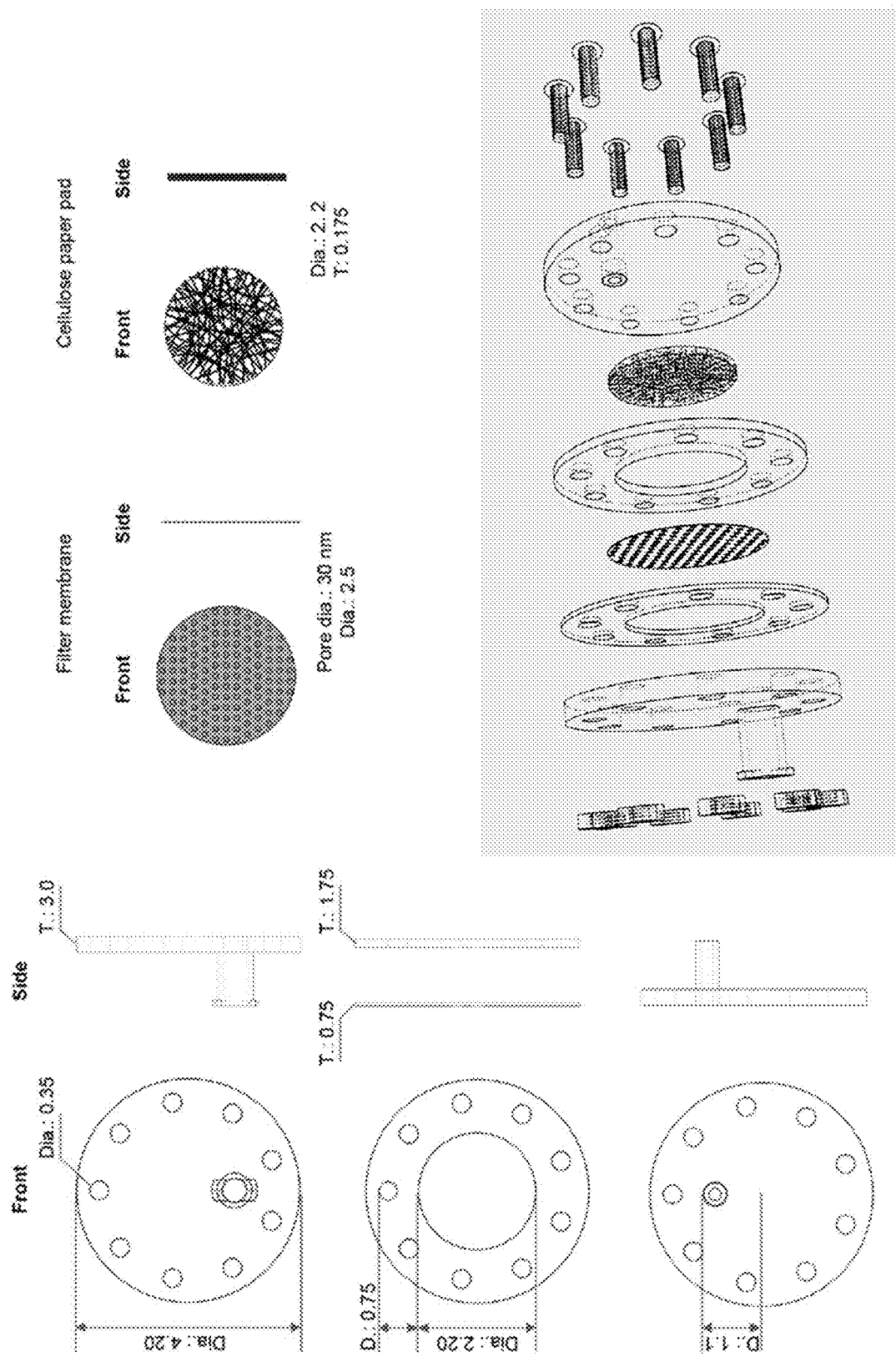
FIG. 5 illustrates the components of an alternative ExoTIC device.

Turning now to FIGS. 4 and 5, exemplary illustrations are shown depicting the structure and construction of the ExoTIC device. FIG. 4 shows the parts of one design while FIG. 5 shows the parts of a slightly different, older design.

Looking at FIG. 4, FIGS. 4a and 4b shows a poly(methyl methacrylate) (PMMA)-based ExoTIC device that has been designed and prepared to isolate exosomes via size-based filtration. The ExoTIC device has a pair of axial plates (which are disc-shaped in the illustrated embodiment), between which ring-like gaskets are captured which secure a membrane (as illustrated, being a low protein binding filter membrane made from track-etched polycarbonate having a 50 nm pore size) and a polyethersulfone (PES) filter (200 nm pore size, as illustrated) in place. The PES filter along with a supportive paper pad (positioned within the inner diameter of the gasket between the filter/membrane and back plate with the outlet) provide structural support for the membrane.

A flow chamber that is collectively defined between the walls of the plates and gaskets. One of the axial plates has an inlet opening, while the other of the axial plates has an outlet opening, with both the inlet opening and the outlet opening being in fluid communication with the flow chamber. The membrane, the filter, and the supportive paper pad are disposed within the flow chamber such that a fluid could not pass from the inlet opening to the outlet opening without passing though the membrane, the filter, and the supportive paper pad. The central axes of the inlet and the outlet openings, as illustrated, are not coincident with one another; instead they are angularly offset from one another (as depicted, approximately 180 degrees from the central axis of the plates) creating some radial travel distance over which the flow of the sample will occur and eliminating a line of direct fluid pressure between the inlet and outlet openings. To create a strong, fluid-tight seal around the periphery, the plates are secured to one another by a ring of compressive fasteners (here, nine bolts and nuts) which encircle the circumference of flow chamber.

With reference to FIGS. 4c and 4d, the various separate components of the exemplary ExoTIC device are illustrated and it can be seen how the ExoTIC device can be built up from these constituent components. As depicted in steps 1 and 2 of FIG. 4c, one of the PMMA plates (the one with the outlet on it) has fasteners inserted through it to form posts which one of the gaskets is received on in step 3. In step 4, the paper pad is inset into the opening of the gasket, such that the back surface of the paper pad contacts the wall of the plate with the outlet opening. In step 5, the PES filter is laid down over the opening of the gasket, with the filter having a diameter slightly larger than the inner diameter of the gasket. The membrane is also laid down over the filter. In step 6, a second gasket is overlaid to capture the membrane and filter between the two gaskets. Then in steps 7 and 8, the opposing plate (with the inlet) is placed over the second gasket and nuts are threaded to the fasteners to compress the plates towards one another and form the assembled ExoTIC device.

It will be appreciated that the described structure above is exemplary in many ways and modifications to this structure are contemplated. As one example, the illustrated plates and gaskets are made from PMMA when, in fact, these components might be made out of any suitable material or materials [for example, other polymers, metals (e.g., aluminum or stainless steel), and/or ceramics]. Still yet, it is contemplated that one or both of the gaskets might be directly formed in the contacting axial plates to form a unitary component or that one or more of the gaskets might be formed of an elastomeric material. Further still, while the end plates are disc-like, it is contemplated that the plates could have other geometries and that other types of fastening systems might be employed other than those depicted. Further still, it will be appreciated that pore sizes on the filter and membrane may be differently selected based on the exosomes to be collected. As will be apparent from the description that follows, modular implementations of the ExoTIC device are contemplated in which a number of ExoTIC devices are placed in series with one another with decreasing pore sizes to collect and filter differently-sized exosomes at each filter. Additionally, in some forms, if the exosome-capturing membrane is sufficiently structurally robust alone, it may be possible to eliminate one or both of the PES filter or paper pad.

When using this ExoTIC device in an exemplary fashion, a sample solution, pre-filtered by a 0.22 µm syringe filter, is introduced continuously into the device at a constant flow rate at the inlet opening one of the axial ends of the chamber as depicted in FIG. 4e using a syringe the introduces the sample into the flow chamber of the ExoTIC device. While a syringe is depicted in the FIG. 4e, it should be appreciated that any other sample-providing device that supplies fluid under pressure into the flow chamber may be used instead with the same practical effect. While the sample is introduced, the polyethersulfone (PES) filter and a paper pad are used to prevent deformation of the nanoporous membrane under the high pressure generated by the syringe pump (having a volume of 10 mL) forces the sample through the flow chamber and out of the outlet. As the sample flows through the flow chamber and as schematically depicted in the detail of FIG. 4b), the exosome vesicles are retained in the chamber in front of the membrane while contaminating small molecules (nucleic acids and proteins) pass the membrane and are removed through the outlet. With the sample being fully forced out of the syringe and through the ExoTIC device (and after washing the low protein binding filter membrane), a regular 200 µL pipet will be inserted into the inlet to retrieve the concentrated exosome preparation with high yield and purity.

Briefly turning to FIG. 5, FIG. 5 illustrates the components of an alternative ExoTIC device. This alternative ExoTIC device is very similar to the ExoTIC device illustrated in FIG. 4, with the primary differences being that a different filter membrane is used, some of the dimensions differ of the components differ slightly, and no supporting PES filter is used.

Cell Culture Exosome Isolation and Purification

The ExoTIC device was subsequently compared to existing exosomic isolation and purification technologies. For purposes of the cell culture studies that follow, the flowing cell culture samples were used.

For the purpose of widespread data analysis, carcinoma epithelial cell lines stemming from various tissues acted as primary candidates for exosome retrieval. Three of the five primary cell strains used: U87 GBM (Glioblastoma), HCC827 (Human lung adenocarcinoma) and H1650 (non-small cell lung cancer), grew in RPMI-1640 (Thermo Fisher Scientific), supplemented identically to DMEM with addition of Sodium Pyruvate (100 mM, Life Technologies). Each strain was routinely detected and treated for Mycoplasma through addition of Plasmocin (prophylactic/treatment, InvivoGen) to prevent potential bacterial RNA and exosome contamination in data retrieval. Each cell line remained monitored closely for confluency and cell death, replaced by an identical frozen vial after 1-2 months.

Cells strains were seeded at 400,000 cells in a 75 $cm^2$ Corning Flask (Canted neck, nonpyrogenic polystyrene) until confluent. Passaging protocols were followed weekly to keep cells healthy. For exosome isolation, each cell strain was seeded in a 6 well Costar cell culture plate at 300,000 cells in media previously indicated. Seeding remains consistent through use of a Cellometer and a Trypan Blue stain to distinguish an accurate live cell count. At 80% well confluency, approximately 2 days from seeding depending on cell type, media in each well is aspirated and replaced with media supplemented by 10% exosome-free FBS from System Biosciences. Replacements of media with exosome-free supplements ensures that the exosomes isolated originated from the desired cell type. After 48 hours, media from each cell type was collected together. The resulting media suspension was then centrifuged at 1,500 g for 10 minutes to pellet any large debris or cells. Supernatant from the centrifugation subsequently passed through a 0.22 µm, 33 mm surface-area Millipore PES membrane filter. Following filtration, the resulting solution can then undergo multiple different isolation protocols. In certain instances, for miRNA comparison analysis, trypsin was added to the wells to detach and pellet the cells for future experimentation.

Isolation of Exosomes from Cultural Media Using the ExoTIC Device

Figure 6:
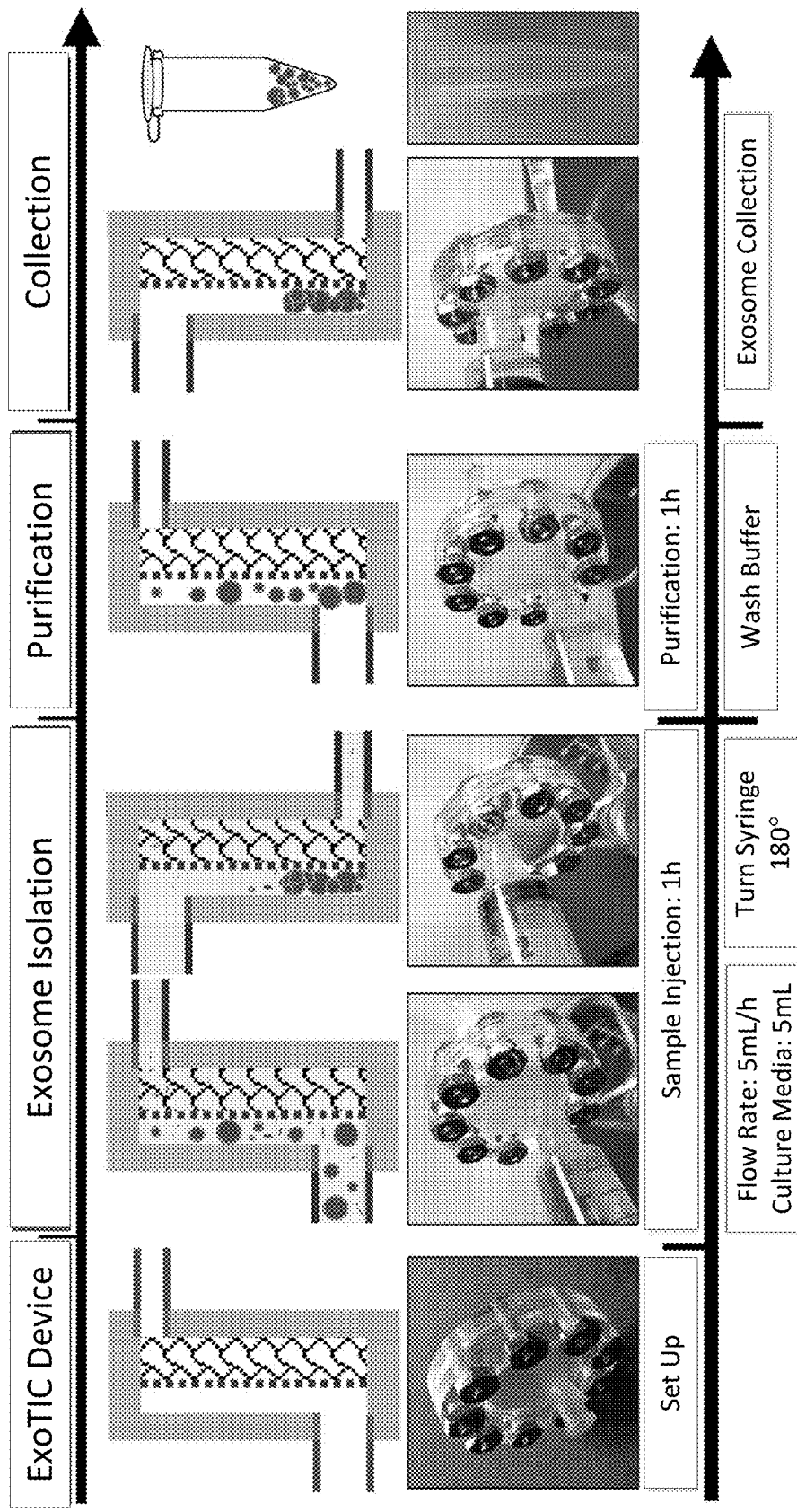
FIG. 6 illustrates the application of ExoTIC device for exosome isolation from cell culture media.

Turning now to FIG. 6, FIG. 6 schematically illustrates the exemplary application of the ExoTIC device for exosome isolation from the cell culture media. The operation of ExoTIC includes isolation from culture media (time consumed by processing 5 mL media, approximately 1 hour), washing with 1×PBS buffer (time consumed by processing 5 mL PBS, approximately 1 hour), and collection of around 200 µL of exosome solution for subsequent analysis.

According to the exemplary protocol, after being assembled or setup, the ExoTIC device is first filtered with 2 mL of 1×PBS buffer by manually pushing a 10 mL syringe or using syringe pump which typically take 5 minutes.

Then, the exosomes from the cultural media may be "enriched" or isolated. The culture media in an amount of 5 mL is pulled in the same syringe and connected with the ExoTIC device again. This syringe along with the ExoTIC device is fixed onto a syringe pump. The outlet of the ExoTIC is fixed on top of the inlet. A pump flow rate of 5 mL/hour is applied for filtering the culture media and enriching exosomes in front of the nanoporous membrane of the ExoTIC device. Free proteins, nucleic acids, cell debris, etc. which are smaller than 50 nm (or whatever the pore size of the membrane is selected to be), can pass through the pores of filter membrane. When about 500 µL of the sample is remaining, the syringe with the ExoTIC device is turned 180° to allow the inlet of the ExoTIC device on top of the outlet to collect exosomes in the chamber of ExoTIC device. Then, pump continues with the same rate until the remaining media is completely filtered.

Next, exosome purification occurs by washing. 1×PBS buffer is used to wash the enriched exosomes inside the ExoTIC device. The empty syringe is disconnected to withdraw 5 mL of 1×PBS buffer and connected with the ExoTIC device again. The syringe with the ExoTIC device is fixed on the pump. Then, the same pumping process from above (washing) is repeated until all the PBS buffer passes through.

At this point, the isolated and purified exosome solution is collected. The ExoTIC device with exosome solution is carefully disconnected from the syringe. A 200 µL pipette is used to retrieve all the exosome solution through the inlet of the ExoTIC device. The purified exosome sample is stored at 4° C. for further molecular analysis.

Ultracentrifugation Isolation Protocol

For the purpose of consistency, 36 mL of cell media prepared in the fashion indicated previously was used for exosome isolation through ultracentrifugation. Cell media was allocated in 2 tubes of polycarbonate centrifuge bottles, developed by Beckman Coulter with a capacity of 26.3 mL each. Both bottles were given 18 mL of cell media and then filled to the brim with PBS to prevent collapse during ultracentrifugation. Each tube was weighed within 0.01 grams of each other and placed within a Type 70 ti rotor inside a Beckman Coulter XL-90 Ultracentrifuge. Tubes were labeled by sharpie to indicated positioning within the motor and help identify the location of the future pellet. Samples were spun at 20,000 g (14000 rpm) for 30 minutes. Debris and molecules with comparatively larger densities than exosomes (i.e. certain microvesicles) were pelleted. Supernatant containing exosomes from each tube was mixed together and temporarily stored in a falcon tube while the centrifuge bottles were thoroughly rinsed and sterilized. Supernatant was then placed back into the bottles, weighed within 0.01 grams, and secured into the rotor once more in identical orientations. The second ultracentrifugation step was run at 100,000 g (31,200 rpm) for 1 hour and 30 minutes. Exosomes, in addition to particles of similar density, were pelleted while proteins and molecules of significantly lesser density stay suspended. Presence of a pellet may or may not be seen depending on cell type and concentration of exosomes, but still present. Once the supernatant is aspirated, the pellet was re-suspended in 100 µL of PBS and stored at −80° C. The centrifuge bottles were once again sterilized and stored for later use.

NanoSight for Profiling Exosome Size and Amount

Exosome samples isolated by one of the two methods previously indicated (along with a third method, ExoQuick-TCT™ available from System Biosciences) were brought to a NanoSight device (NS300, Malvern Instruments Limited of Malvern, UK) for size profiling. To prevent significant aggregation, samples were warmed to room temperature and vortexed before being diluted in series to fit a 30-100 particles/frame screen display. For exosome samples prepared from culture media, 10 µL of exosome solution is diluted 100× for NanoSight analysis. For the exosome samples prepared from plasma (as will be discussed below in regards to other verifying studies), 10 µL of plasma exosome solution is diluted 500× for NanoSight analysis.

NanoSight software parameters were adjusted to give a bin size of 1 nm as well as a line jump distance of 16 and target temperature of 25° C. Auto-setup on the NanoSight allowed for a fine-tuned adjustment of parameters closely located at the values recently stated. Samples were passed through the NanoSight one at a time, with a series of washes with ethanol and PBS between each. Data analysis was taken in triplicates and exported as a series of excel file data points, pdf graphs, and video recordings of each sample.

Evaluation of Exosomes from Culture Media Using Exotic and Ultracentrifugation:

The performance of the ExoTIC device was evaluated by isolating exosomes from culture media by comparing results to the ultracentrifugation isolation protocol and the ExoQuick-TCT™. The identity of isolated exosomes was confirmed by their size distribution using dynamic light scattering (NanoSight NS300, described in the section above). Moreover, the morphology and size of the purified exosomes were also confirmed by scanning electronic microscopy (SEM).

Figure 7:
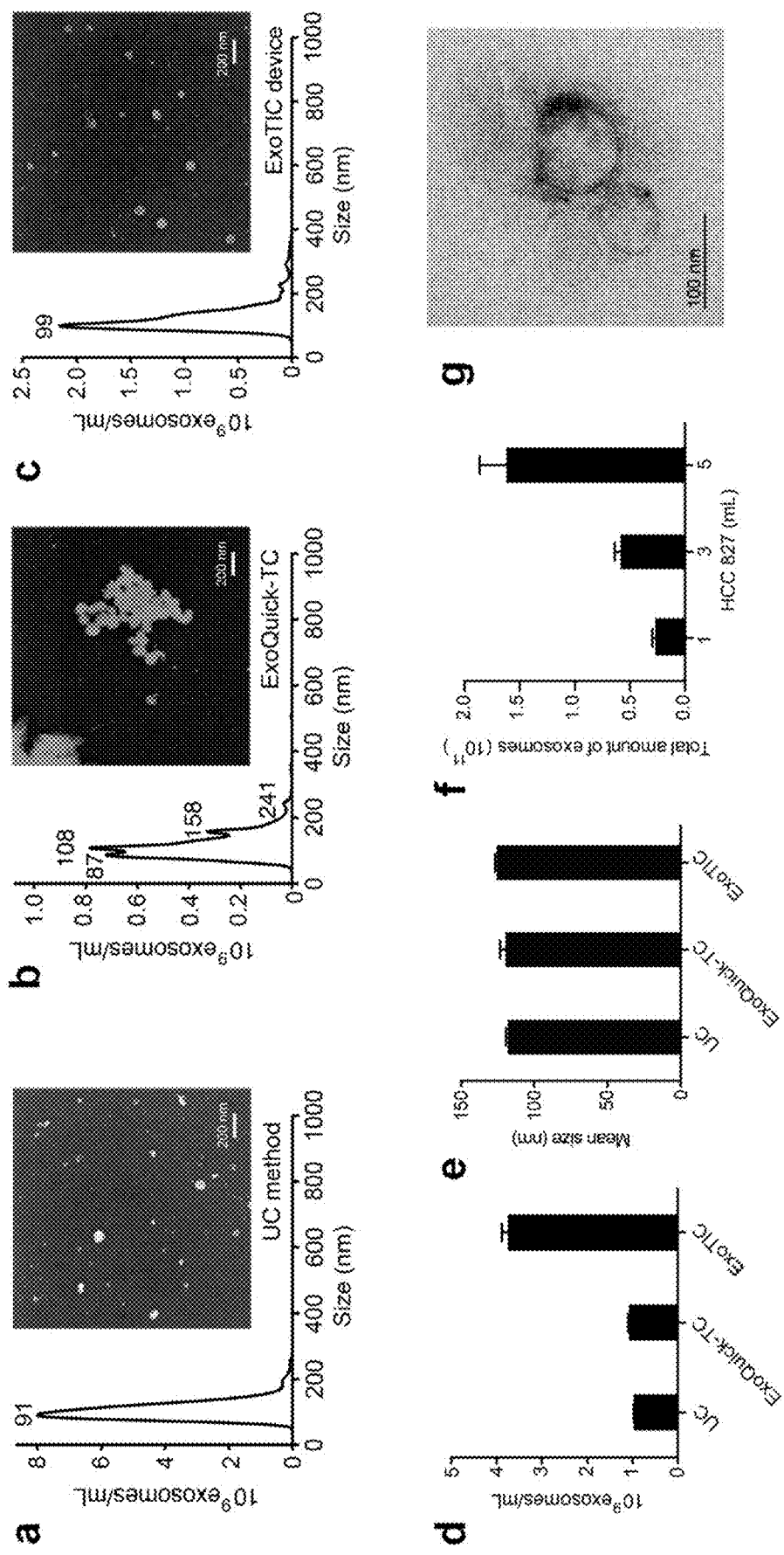
FIG. 7 illustrates the characteristics of exosomes isolated from culture media using an ExoTIC device.

As can be seen in FIG. 7, exosomes isolated using ultracentrifugation method had a mode (peak) size of 91 nm (FIG. 7a, NanoSight profile) and uniform size with diameters around 100 nm (FIG. 7a, SEM inset). The exosomes purified by the ExoQuick-TC Kit formed aggregates with multi-mode sizes (FIG. 7b). The exosomes isolated by the ExoTIC device had a mode size of 99 nm (FIG. 7c, NanoSight profile) and a size distribution from 30 to 200 nm (FIG. 7c, SEM inset).

As illustrated in FIG. 7d, the ExoTIC device showed a four-fold higher yield of exosomes isolated from culture media when compared with the ultracentrifugation method. The mean size of the exosomes purified by the three methods were consistently around 120 nm as illustrated in FIG. 7e. FIG. 7f provides a comparison of the total amount of exosomes purified from different volumes of HCC827 cell culture medium using the ExoTIC device. The ExoTIC device can recover exosomes from culture media with a volume ranging from 1 to 5 mL. The TEM image in FIG. 7g shows lipid bilayer structure of exosomes using the ExoTIC device.

These results demonstrated that the ExoTIC device can efficiently isolate exosomes from culture media with a wide size distribution without damage on the physical structure and avoiding the polymer contaminants.

Molecular Characterization of Exosomes Isolated with ExoTIC Device

Figure 8:
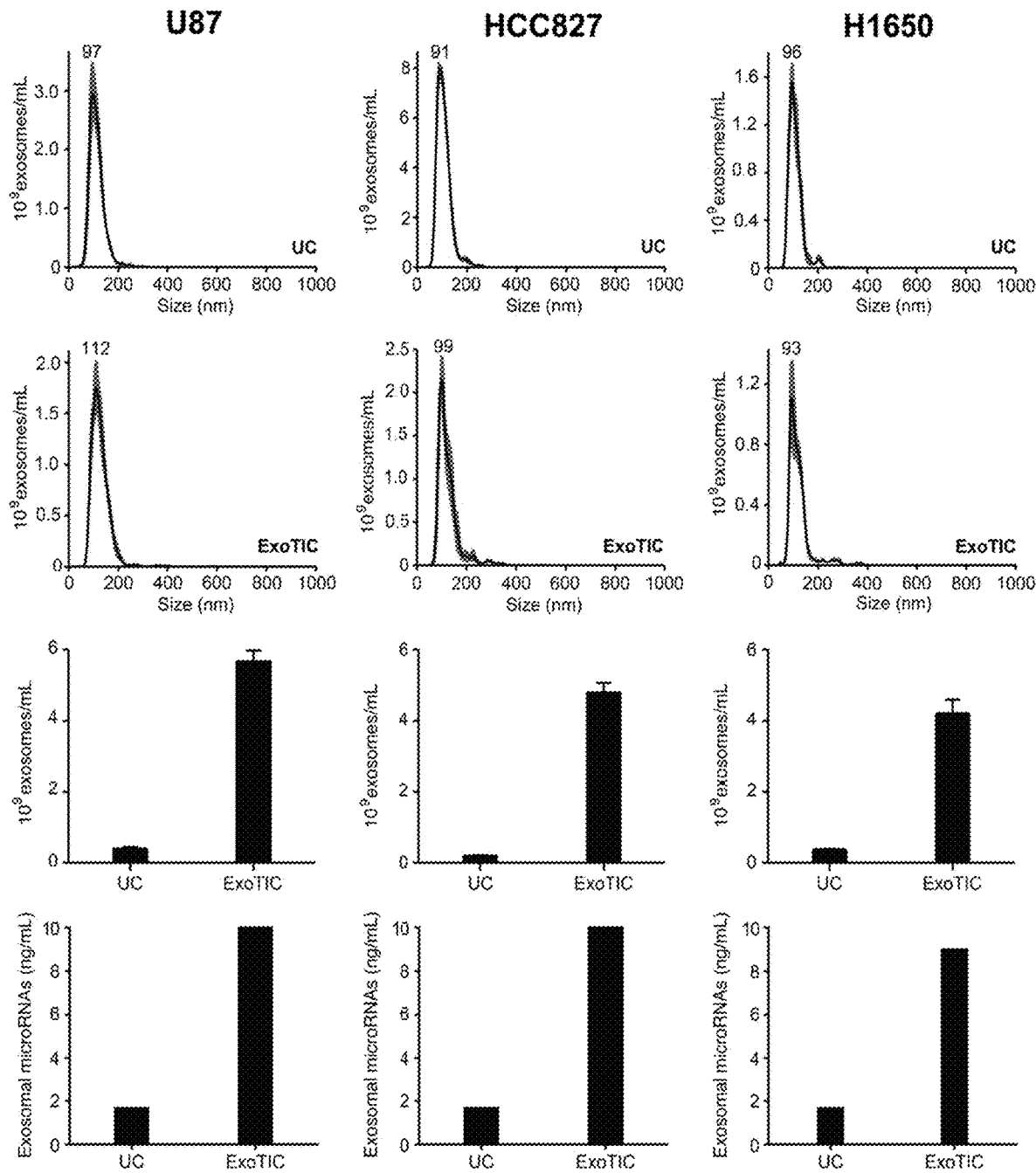
FIG. 8 includes various charts illustrating the quantification of exosomal microRNAs.

Turning now to FIG. 8, quantification of exosomal microRNAs is provided. Isolated exosomes using the ExoTIC device compared to traditional ultracentrifuge (UC) methods are shown in three separate cancer cell lines U87 (Brain) HCC 827 (Lung) and H1850 (Lung). Size distribution is shown in the top rows for UC vs ExoTIC. In the bottom two rows, comparative exosome and RNA quantities are shown for UC vs ExoTIC. Collectively this data indicates that the ExoTIC device captures a similar population compared to traditional isolation techniques like ultracentrifuge with better yields.

Thus, the ExoTIC device was demonstrated to equivalently capture exosomes from 3 cell lines' media collected from Gliobastoma Multiforme (U87) and lung cancer patients (HCC 827, H1850) in comparison to conventional ultracentrifuge techniques. Similarly-sized exosomes can be recoved using the ExoTIC device as in comparison to ultracenterfuge. As can be seen in the third row of FIG. 8, exosome yields from 5 mL of culture media were respectively four to six-fold higher for the ExoTIC device compared to ultracentrifuge. As can be seen in the fourth row of FIG. 8, microRNA profiles of exosomes derived from 10 mL of culture media using the ExoTIC device and 60 mL of the same culture media using ultracentrifuge were similar.

NanoString™ Quantification of Exosomal microRNA

Figure 9:
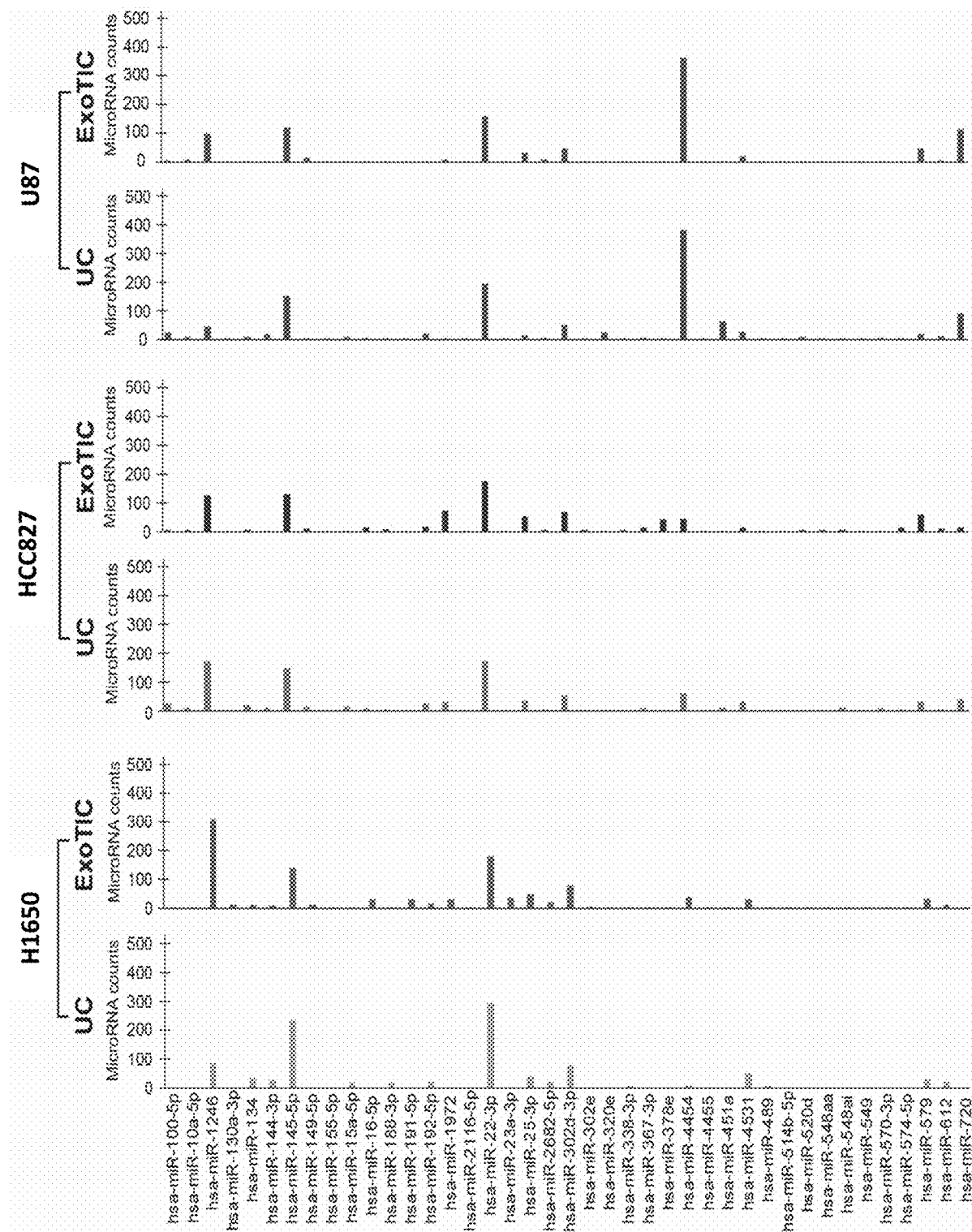
FIG. 9 illustrates the quantification of exosomal RNAs using NanoString.

FIG. 9 illustrates the quantification of exosomal RNAs using NanoString™. The exosomes of U87 (glioblastoma), HCC827 (lung cancer), and H1650 (lung cancer) cell lines were isolated by the ExoTIC device and ultracentrifugation method.

We further analyzed the microRNA analysis content of the isolated exosomes using over 800 microRNAs detected by absolute quantitation using fluorescent tags and digital imaging (NanoString™) and showed comparable quantification as observed in ultracentrifugation. The top 10 microRNAs detected from the supernatant of cell lines shown above (U87, HCC827, H1850) using the NanoString™ genome wide microRNA assay are shown. The ExoTIC device detected these microRNAs in a similar quantity compared to ultracentrifugation (UC). The average across the three cell lines is displayed per microRNA by method of isolation.

Modular Function of ExoTIC Device

Cells release different size extracellular vesicles, especially for exosomes with size range from 50 to 150 nm, but it is not known which sizes of exosome carry the key biomolecular signature and play the most important roles on cell to cell communications.

Figure 10:
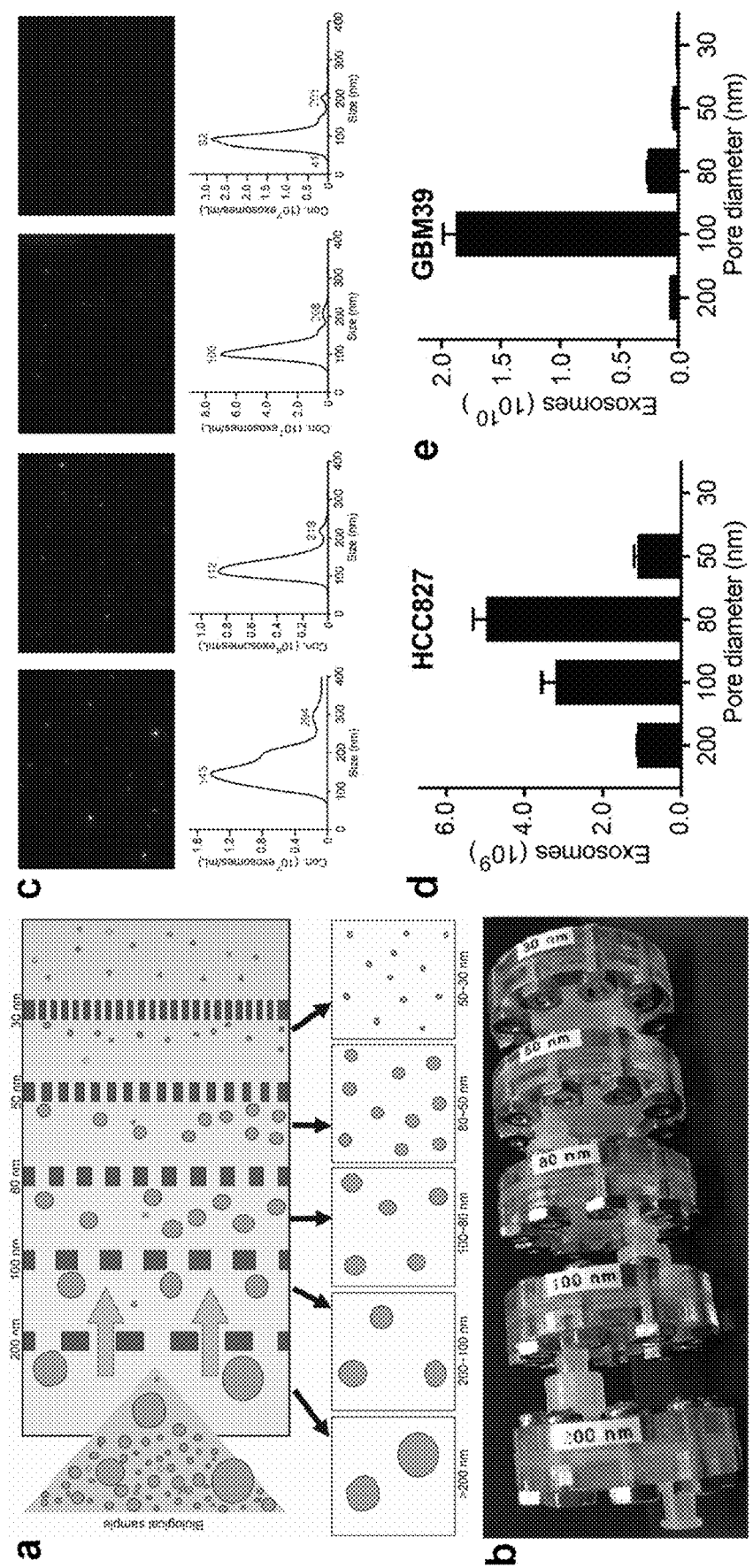
FIG. 10 illustrates the modular function of the ExoTIC device for isolation of specific size exosomes.

Turning now to FIGS. 10a and 10b, modular function was demonstrated by connecting several ExoTIC devices in series with different membranes (pore dia. 200, 100, 80, 50, and 30 nm, respectively) for simultaneous injection and specific isolation of exosomes with narrow size ranges from same bio-fluids. Effectively, this modular design can result in the capture of groups of exomes in which each of the groups has a different size.

To validate this modular design, 5 mL culture media of HCC 827 cell line was injected with a flow rate of 5 mL/h, and then 10 mL of 1×PBS buffer was injected for washing. The isolated exosome samples were collected from the 200 nm to 30 nm ExoTIC sites (one-by-one) and saved in 1.5 mL of Eppendorf tubes. Then, as depicted in FIG. 10c, NanoSight analysis was performed to characterize the amount and size of exosomes that were collected. The NanoSight results show that the sizes of exosomes are gradually reducing. The size and amount distributions between HCC 827 cell line and GBM 39 cell line were also compared and the results are provided in FIGS. 10d and 10e. Exosomes with diameter less than 50 nm were not observed for both cell lines. The higher number of exosomes for HCC 827 cell line appeared with sizes ranging between 100 and 80 nm, and for GBM 39 cell line exosome sizes ranged between 200 to 100 nm. Hence, application of this modular function, the ExoTIC device shows a potential for studying and comparing the size and amount for various cancer, cell line, and sample types.

Still further, it is contemplated that the modular design can be used to process large volumes of samples by running the ExoTIC device in parallel.

Protocol for Exosome Isolation from Human Plasma Using the ExoTIC Device

Figure 11:
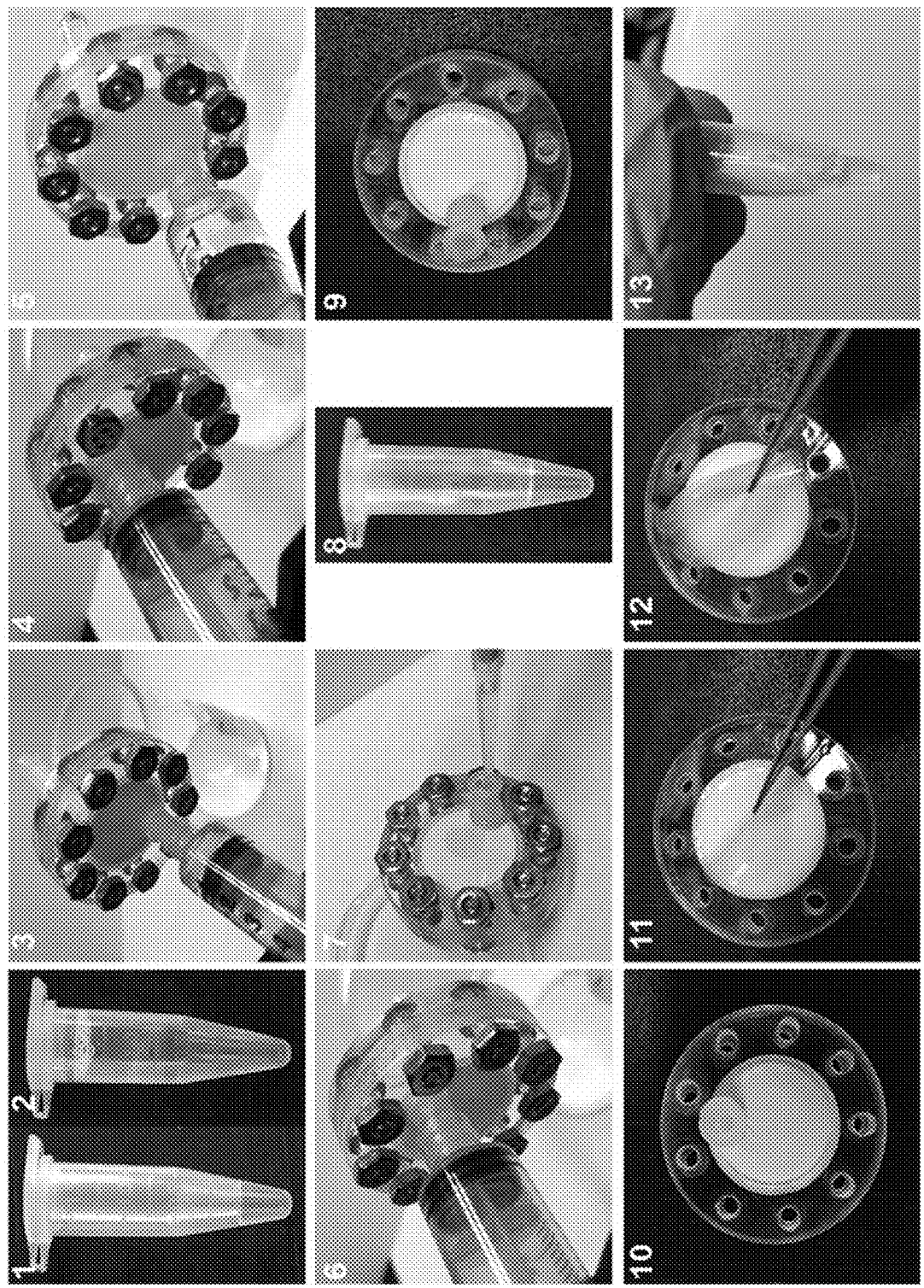
FIG. 11 illustrates the steps of isolating exosomes from human plasma using an ExoTIC device.

FIG. 11 illustrates exosome isolation from human plasma using the ExoTIC device.

First, plasma is collected from human blood. This step takes approximately 30 minutes. In the instant case, the Life Technologies' protocol was followed to prepare plasma from human blood received from the Stanford Blood center. 1 mL of blood in each 1.5 mL microtube is centrifuged at 1,000 g for 10 min to remove blood cells, using a refrigerated centrifuge. The collected plasma is further centrifuged at 2,000 g for 15 min to deplete platelets in the plasma samples. A resultant 100 µL plasma in a 1.5 mL microtube is illustrated at (1) in FIG. 11.

The next step for preparation of plasma samples takes 5 minutes. 400 µL of 1×PBST (Tween 20 0.05%) buffer is added into 100 µL plasma and pipetted for full mixing. Then the 500 µL plasma PBST mixture is filtered with the lowest protein binding syringe filter (pore size: 200 nm) to remove all the things with size larger than 200 nm, and the flow through is collected with a 1.5 mL microtube. Further, 1 mL of 1×PBST buffer, 1×PBS buffer, or DI water is used to wash the syringe filter and the flow through is collected in the same microtube. A 1 mL pipette is used to mix the plasma PBST or PBS solution. This produces 1.5 mL of filtered plasma in PBST or PBS solution as depicted in panel (2) of FIG. 11.

Exosome isolation takes approximately 1 hour. About 1.5 mL of plasma PBST or PBS solution is sucked up by a 10 mL syringe and connected with the ExoTIC device. After being fixed onto a syringe pump, a pumping rate of 1.5 mL/h is applied to enrich exosomes in the ExoTIC device and remove free proteins, nucleic acids, and cell debris as depicted in panel (3). When about 500 µL is left, the syringe with the ExoTIC device is turned 180°, so the inlet of the ExoTIC device is on top of outlet as depicted in panel (4), to collect exosomes in the chamber of the ExoTIC device. After turning, the pumping continues at same rate until the remaining media is completely filtered.

Exosome purification takes approximately 1.5 hours. 1×PBS buffer or DI water is used to wash the enriched exosomes inside of the ExoTIC device. The empty syringe is disconnected and sucked up 3 mL of 1×PBS buffer or DI water and connected with the ExoTIC device again as depicted in panel (5). The syringe with ExoTIC device is fixed on the pump. Then the same pumping process performed during the presentation of the sample is repeated until all the PBS buffer pass through. Again, the syringe and the ExoTIC device are rotated part way through, as depicted in panel (6).

Collecting the exosome solution takes approximately 5 minutes. The ExoTIC device with exosome solution is carefully disconnected from the syringe. As depicted in panel (7), a 200 μL size pipette is used to take out all the exosome solution through the inlet of the ExoTIC device. The collected exosome liquid sample is kept in a 1.5 mL microtube as depicted in panel (8) and stored at 4° C. for further analysis.

Although it will not be described in great detail, the membrane can be recovered as is generally depicted in panels (9)-(13). The filter from can be put into the obtained exosome solution as depicted in panel (13) and vortex for 1 minute.

Isolation of Exosomes from Healthy Human Plasma Samples

Figure 12:
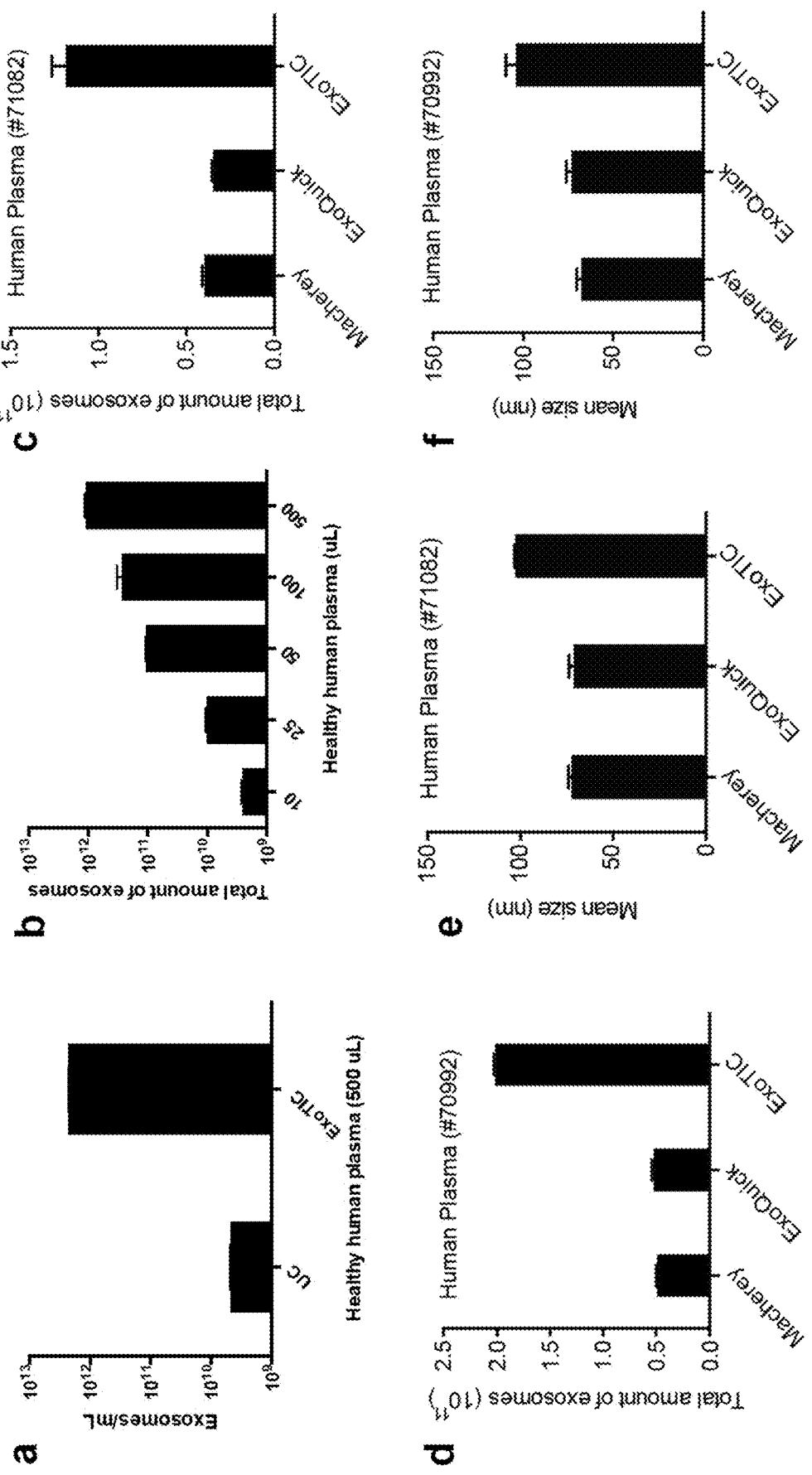
FIG. 12 shows the comparative results of isolation of exosomes from healthy human plasma samples.

The results of exosomes isolated from healthy plasma samples have been compared with the existing methods published in the literature (ultracentrifugation, Macherey, and ExoQuick). In the ExoTIC's results, compared to ultracentrifugation, the exosome yield purified from small volume (500 μL) of healthy human plasma by the ExoTIC device is 1,000 times higher than that by the UC method as illustrated in FIG. 12a. The isolation efficiency of the ExoTIC device was also validated in processing 10 to 500 μL of healthy human plasma samples as established by the results shown in FIG. 12b. Compared with commercial kits (Macherey and ExoQuick), in FIGS. 12c and 12d, the ExoTIC device showed three and four-fold higher yield of exosomes isolated from healthy plasma of two patients (patient #71082 and patient #70992), respectively. FIGS. 12e and 12f show that the mean size detected by the ExoTIC device was somewhat greater than that detected by the other two commercial kits.

Isolation of Exosomes from Various Types of Cancer Samples

Figure 13:
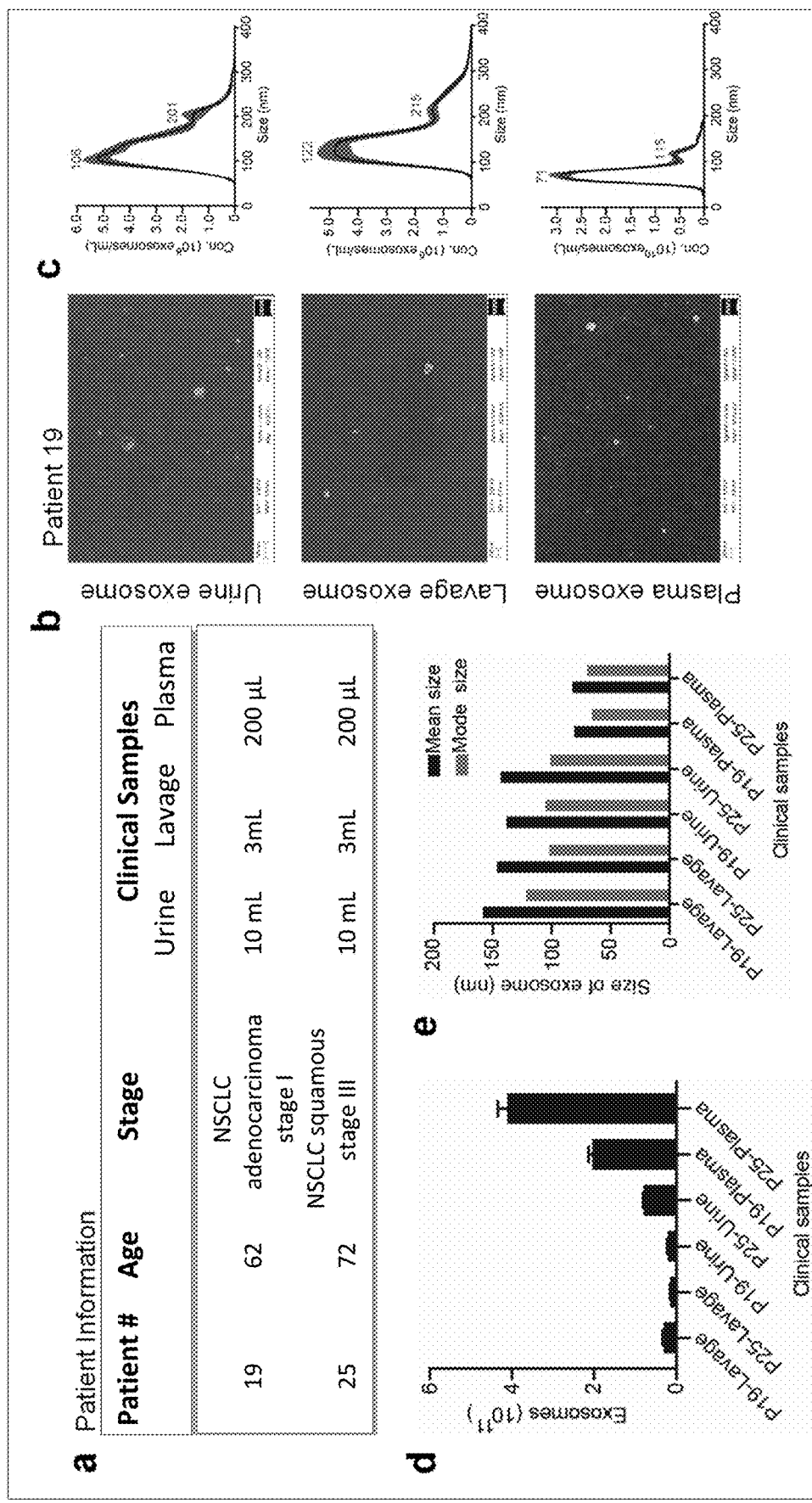
FIG. 13 illustrates the isolation and characterization of exosomes from various types of clinical cancer samples.
Figure 14:
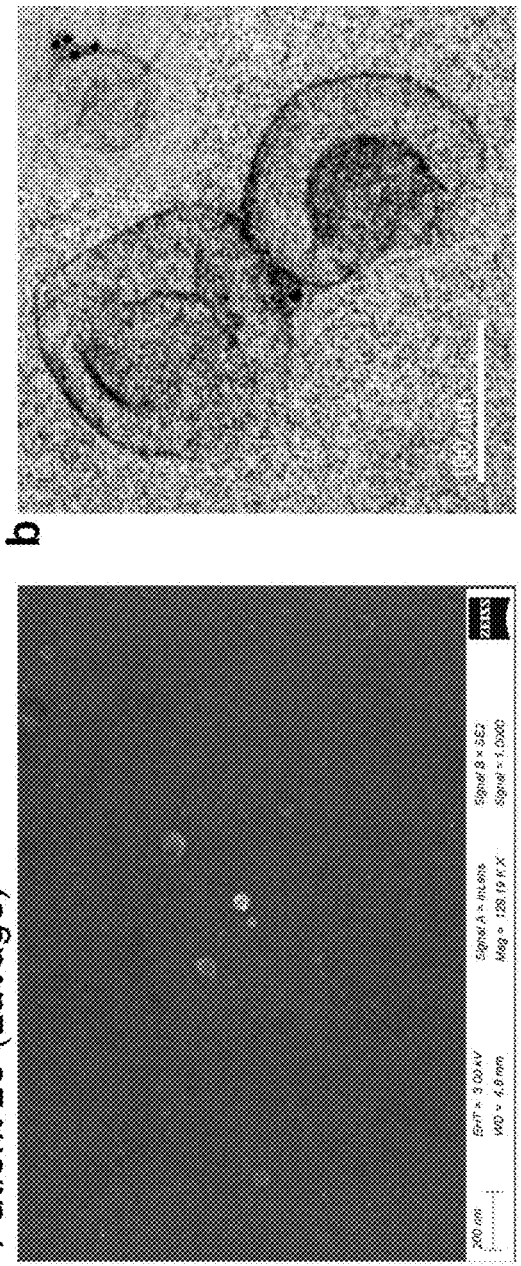
FIG. 14 provides SEM and TEM images of lavage and plasma samples from patient #25.
Figure 14:
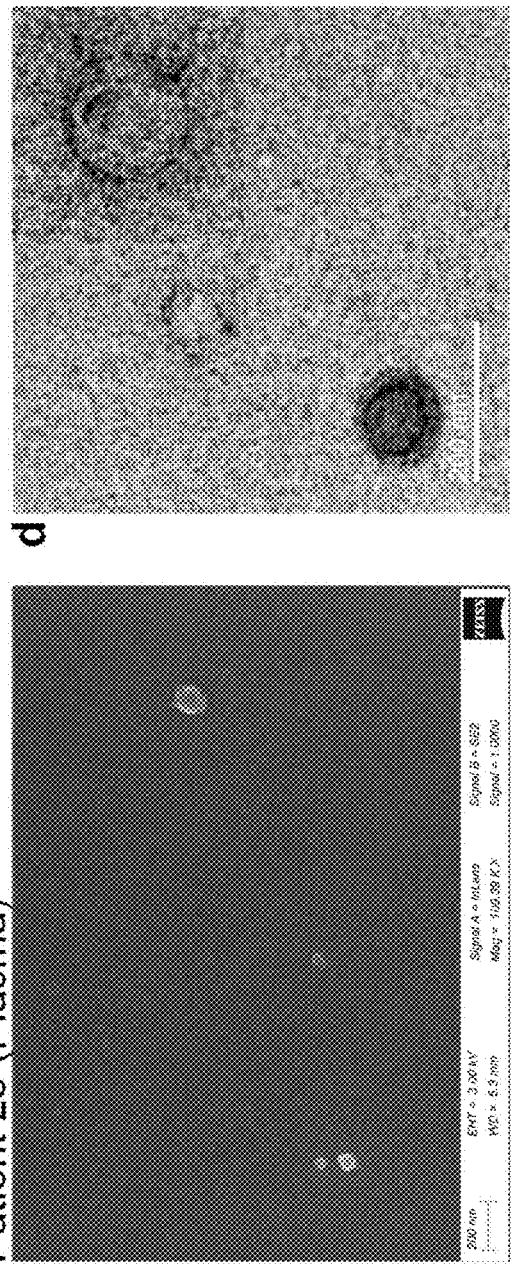

It was observed that purified exosomes could be reproducibly and efficiently isolated from urine, lavage, and plasma samples of two patients (#19 and #25) with non-small cell lung cancer (NSCLC) as profiled in FIG. 13a. FIGS. 13b and 13c, respectively show the SEM images and size range of exosomes recovered from urine, lavage, and plasma samples of patient #19. As can be seen in FIG. 13b, the sizes of isolated exosomes ranged from about 40 nm to 120 nm in diameter. From FIG. 13d, it can be seen that the amounts of exosomes present in the patient plasma samples (of both patients #19 and #25) are significantly higher than those in the lavage and urine. From FIG. 13e, it can be seen that the mean sizes of exosomes isolated from lavage and urine samples (dia. ~150 nm) are larger than the plasma samples (dia. ~75 nm) from same patients. FIG. 14 provides SEM and TEM images of lavage and plasma samples from patient #25.

TEM of Exosomes from Various Types of Cancer Samples

Figure 15:
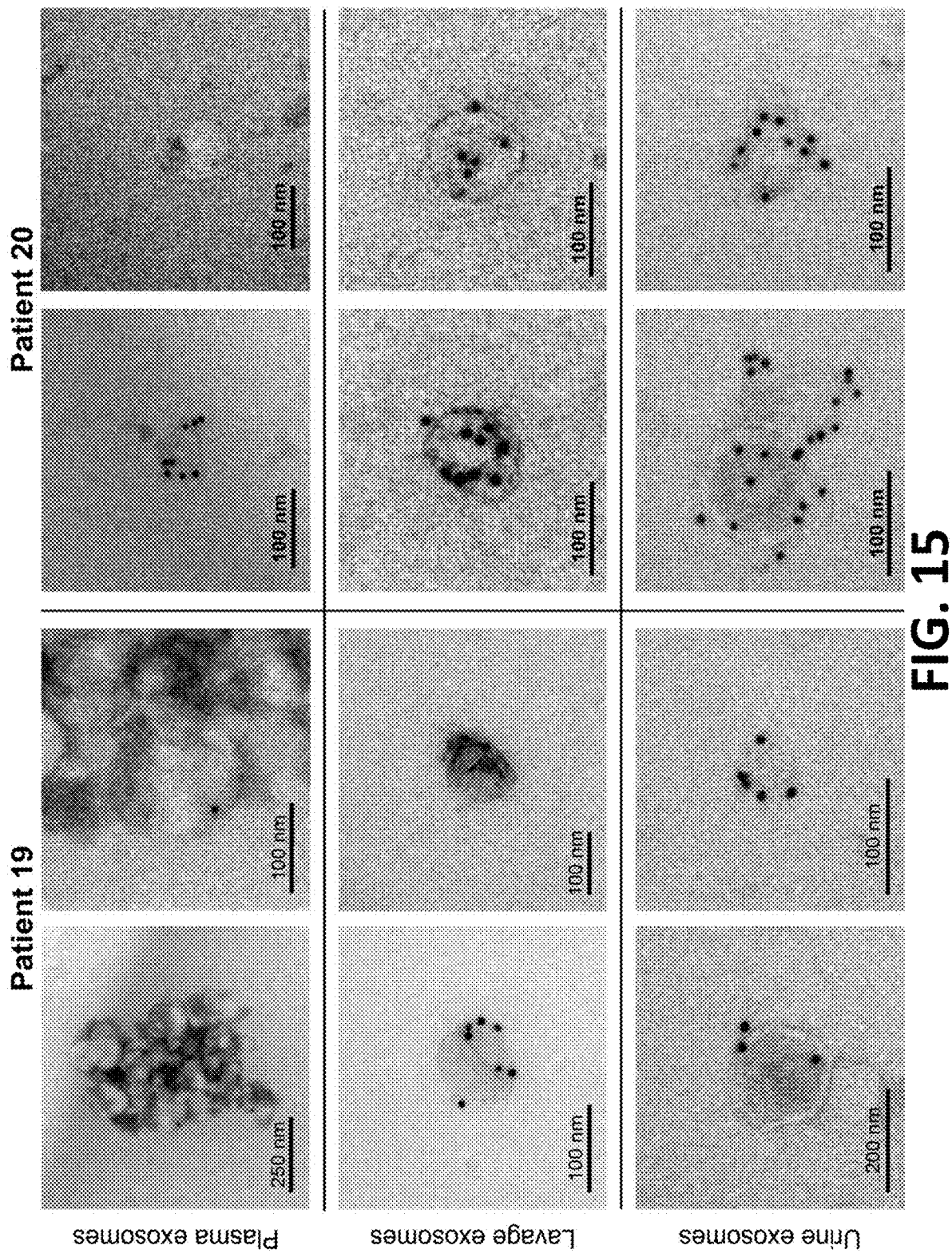
FIG. 15 includes TEM images illustrating the characteristics of exosomes using immuno-GNP-CD63 (GNP dia. 10 nm) antibody including exosomes isolated from plasma, lavage and urine samples of two patients.

The isolated exosomes in terms of size and morphology of two patients (#19 and #20) were further evaluated using TEM as shown in FIG. 15 which shows TEM images of plasma, lavage, and urine exosomes for each of these two patients.

The description of how the samples were prepared for imaging and how the samples were imaged follows. Carbon coated copper grids (Ted Pella Inc.) were glow discharged. All solutions were applied to the membrane coated side of the grids. This side was kept wet until the end of the preparation, while the reverse was kept dry. First, a 5 μL drop of the fixed exosome solution was placed on the grid, and allowed to incubate for 20 minutes while covered. Next, washing and blocking was performed by floating each sample face down in 100 μL drops of the following solutions: PBS (2×, 3 minutes each), PBS/50 mM glycine (4×, 3 min.), PBS/5% BSA (1×, 10 min.). A 20 μg/ml solution of mouse anti-human CD63 antibody Clone TS63 (Abcam) was used for labeling (1 hour), followed by six-time wash in PBS/0.5% BSA. Samples were incubated in a 1:50 dilution of rabbit anti-mouse immunogold conjugates (Sigma) in 5% BSA/PBS (20 min.) and washed in PBS (6×) followed by water (6×). Finally, negative staining of the membranes was achieved using a 1:9 ratio mixture of 2% methylcellulose and 4% uranyl acetate (10 min.). Excess liquid was wicked away using Whatman No. 1 filter paper, leaving a thin layer behind to dry. Imaging was performed in an FEI Tecnai TEM operated at 200 kV. The morphology and size information and the presence of the exosome-specific surface marker CD63 available from the high-resolution images of TEM convincingly prove that the organelles isolated by the ExoTIC device are exosomes.

Bioanalyzer Results from Plasma

Figure 16:
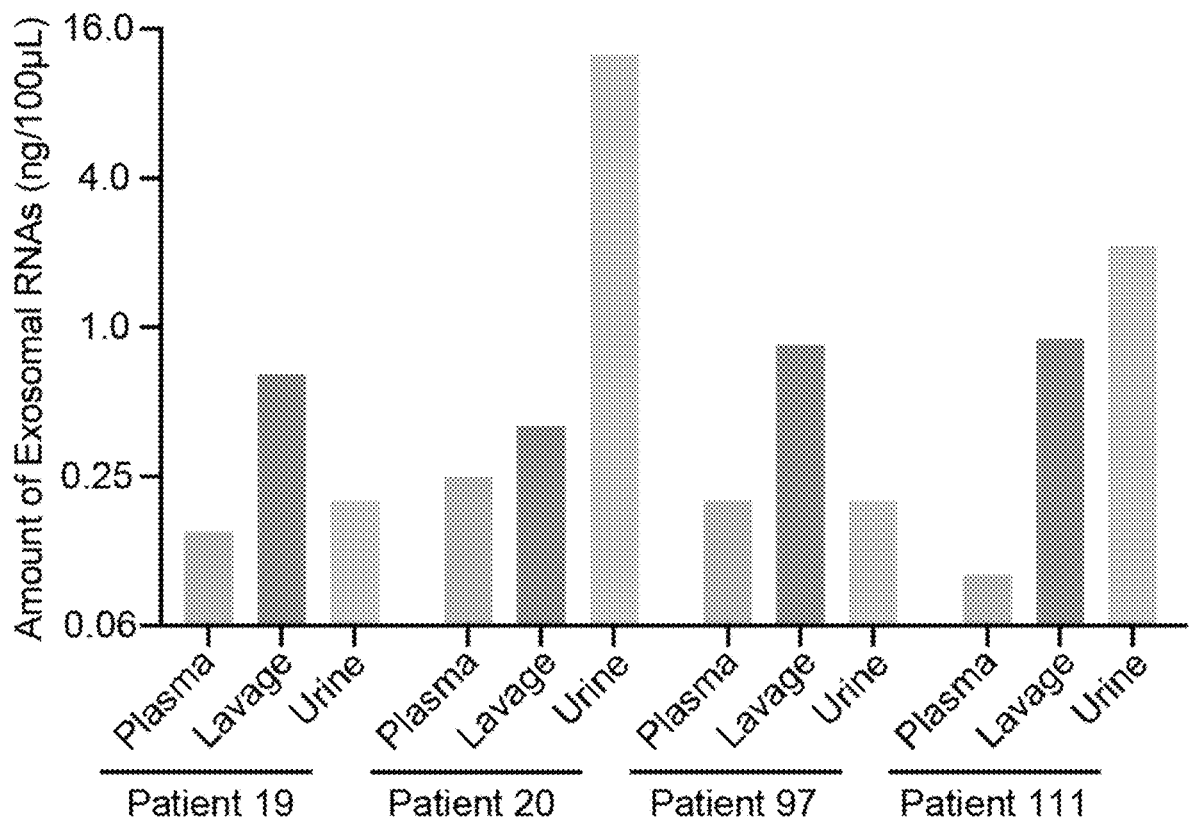
FIG. 16 illustrates the amount of exosomal RNAs extracted from plasma, lavage, and urine samples of four patients.

FIG. 16 provides bioanalyzer results from the plasma, lavage, and urine samples of four patients with lung cancer for which clinical information and sample information is provided in Tables 2 and 3 below:

TABLE 2

Clinical information of patients with lung cancer

| Study ID | IRB | Final diagnosis | BAL Aliquots | Plasma Aliquots | Urine (cc) | For Batch | Total Fractions |
|---|---|---|---|---|---|---|---|
| 19 | 34235 | Malignant | 2 | 1 | 40 | Y | 6 |
| 20 | 34235 | Malignant | 2 | 1 | 13 | Y | 6 |
| 97 | 27791 | Malignant | 2 | 2 | 15 | Y | 6 |
| 111 | 27791 | Malignant | 2 | 1 | 20 | Y | 6 |

TABLE 3

Clinical information of patients with lung cancer for exosome isolation

| Sample Key List | Sample | IRB | Volume |
|---|---|---|---|
| 1 | Patient-19-Plasma | 34235 | 400 uL |
| 2 | Patient-19-lavage | 34235 | 2.5 mL |
| 3 | Patient-19-Urine | 34235 | 10 mL |
| 4 | Patient-20-Plasma | 34235 | 500 mL |
| 5 | Patient-20-lavage | 34235 | 2.0 mL |
| 6 | Patient-20-Urine | 34235 | 10 mL |
| 7 | Patient-97-Plasma | 27791 | 500 mL |
| 8 | Patient-97-lavage | 27791 | 2.4 mL |
| 9 | Patient-97-Urine | 27791 | 10 mL |
| 10 | Patient-111-Plasma | 27791 | 600 mL |
| 11 | Patient-111-lavage | 27791 | 2.0 mL |
| 12 | Patient-111-Urine | 27791 | 10 mL |

Looking at FIG. 16, the bioanalyzer results show that exosomes isolated from plasma have the lowest amount of RNAs, even when the exosome yield is high. Lavage exosomes from different patients showed similar amount of RNAs. The amount of RNAs from urine samples vary more greatly from patient to patient.

Thus, an ExoTIC device and various related methods of use are disclosed herein. It is contemplated that this device and related methods of use can be applied to a large number of applications, some of which will now be listed in a non-limiting exemplary fashion. For example, it can be used in the isolation of exosomes from different types of biofluids including plasma, serum, saliva, lavage, culture media and urine. Further still, it could be used in the identification of exosome based nucleic acid biomarkers and protein biomarkers for cancer detection.

Indeed, the ExoTIC device may be broadly applicable to fundamental and clinical research in the field of oncology (e.g., lung, breast, ovarian, and prostate cancer). The ExoTIC device holds great promise as a universal platform to profile exosomes from a broad range of sample types (e.g., saliva, serum, blood and urine) that have previously been shown to contain tumor specific exosomes in patients suffering from lung cancer or other cancers. The ExoTIC device could significantly improve the exosome-based early detection of lung cancer and benefit patients with cancer. Implementation of the ExoTIC device could enable the discovery of new lung cancer biomarkers and increase our understanding of the molecular mechanisms driving progression to clinically significant lung cancers and their various subtypes. Still yet, implementation of the ExoTIC device for clinical diagnosis could help differentiate between responders and non-responders and predict susceptibility to drug treatment. Still further, it will be appreciated and recognized by those having skill in the art that while the isolation of exosomes using the ExoTIC device has been demonstrated specifically above that the ExoTIC device and associated methods of use can be used to capture any extracellular vesicle including, but not limited, to exosomes.

The present invention has been described in terms of one or more preferred embodiments, and it should be appreciated that many equivalents, alternatives, variations, and modifications, aside from those expressly stated, are possible and within the scope of the invention. As some not-limiting examples of modifications, it is contemplated that the ExoTIC device (gasket thickness, membrane diameter) and the isolation procedure (flow rate, ionic strength of wash buffer, wash buffer detergent) could be further optimized to increase yield and purity of exosome isolations.

What is claimed is:

1. A device for isolation of extracellular vesicles from an extracellular vesicle-containing sample, the device comprising:
    a flow chamber having an inlet and an outlet which are placed in fluid communication with one another by the flow chamber; and
    a membrane disposed in the flow chamber such that a fluid flowing from the inlet to the outlet through the flow chamber must pass through the membrane, the membrane adapted to collect extracellular vesicles from an extracellular vesicle-containing sample thereon while permitting a remainder of the extracellular vesicle-containing sample to flow through to the outlet.

2. The device of claim 1, wherein the extracellular vesicles are exosomes.

3. The device of claim 2, further comprising at least one supportive backing layer between the membrane and the outlet.

4. The device of claim 3, wherein the at least one supportive backing layer comprises a paper pad.

5. The device of claim 4, wherein the at least one supportive backing layer further comprise a filter between the membrane and the paper pad.

6. The device of claim 5, wherein the membrane has a porosity with an average pore diameter selected from the group of 30 nm, 50 nm, 80 nm, 100 nm, 200 nm, 1000 nm, and 5000 nm.

7. The device of claim 6, wherein the filter has an average pore diameter of 200 nm.

8. The device of claim 2, wherein the flow chamber is defined by a pair of opposing plates fastened together to secure the membrane in place therebetween, one of the pair of opposing plates providing the inlet and the other of pair of opposing plates providing the outlet.

9. The device of claim 8, further comprising a pair of gaskets positioned between the plates in which the membrane is secured between the pair of gaskets.

10. A modular device for isolation of extracellular vesicles from an extracellular vesicle-containing sample, the modular device comprising several devices for extracellular vesicle isolation according to claim 1 in series with one another, connecting the outlet of one of the devices to the inlet of another one of the devices, in which each of the several devices for extracellular vesicle isolation has a membrane with a different porosity than at least some of the others.

11. The modular device of claim 10, wherein the membranes of each of the several devices have decreasing average pore diameters from the inlet of a first device to the outlet of the last device.

* * * * *

UNITED STATES PATENT AND TRADEMARK OFFICE
CERTIFICATE OF CORRECTION

PATENT NO. : 11,761,952 B2
APPLICATION NO. : 17/345968
DATED : September 19, 2023
INVENTOR(S) : Fei Liu et al.

It is certified that error appears in the above-identified patent and that said Letters Patent is hereby corrected as shown below:

In the Specification

Column 12, Line 16, "TCT™" should be --TC™--.

Column 12, Line 41, "Quick-TCT™" should be --Quick-TC™--.

Column 16, Table 3, Line 42, "1RB" should be --IRB--.

Signed and Sealed this
Nineteenth Day of December, 2023

Katherine Kelly Vidal
Director of the United States Patent and Trademark Office